United States Patent
Yamamoto et al.

(10) Patent No.: US 10,791,914 B2
(45) Date of Patent: Oct. 6, 2020

(54) INSERTION/REMOVAL SUPPORTING APPARATUS AND INSERTION/REMOVAL SUPPORTING METHOD

(71) Applicant: OLYMPUS CORPORATION, Tokyo (JP)

(72) Inventors: Eiji Yamamoto, Musashimurayama (JP); Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 470 days.

(21) Appl. No.: 15/626,487

(22) Filed: Jun. 19, 2017

(65) Prior Publication Data

US 2017/0280978 A1 Oct. 5, 2017

Related U.S. Application Data

(63) Continuation of application No. PCT/JP2014/083747, filed on Dec. 19, 2014.

(51) Int. Cl.
*A61B 1/00* (2006.01)
*A61B 1/005* (2006.01)
(Continued)

(52) U.S. Cl.
CPC ........ *A61B 1/00167* (2013.01); *A61B 1/0051* (2013.01); *G01D 5/35341* (2013.01);
(Continued)

(58) Field of Classification Search
CPC ............. A61B 1/00167; A61B 1/0051; A61B 2034/2046; A61B 2034/2061; G01D 5/35341
See application file for complete search history.

(56) References Cited

U.S. PATENT DOCUMENTS

2009/0221869 A1* 9/2009 Tanaka ................ A61B 5/06
600/103
2011/0319714 A1* 12/2011 Roelle ................ A61B 1/00006
600/118
(Continued)

FOREIGN PATENT DOCUMENTS

CN 1694643 A 11/2005
JP H06-154153 A 6/1994
(Continued)

OTHER PUBLICATIONS

English translation of International Preliminary Report on Patentability dated Jun. 29, 2017 together with the Written Opinion received in related International Application No. PCT/JP2014/083747.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

A supporting apparatus for supporting insertion of a flexible insertion member into a subject and removal of the insertion member includes an attention point acquisition unit, a first displacement acquisition unit and a determination unit. The attention point acquisition unit specifies at least one first attention point specified by a shape of the insertion member. The first displacement acquisition unit acquires a first displacement of the first attention point. The determination unit determines how a state of the insertion member or the subject is at a position corresponding to the first attention point, based on displacement information including information on the first displacement.

12 Claims, 30 Drawing Sheets

(51) Int. Cl.
  *A61B 34/20* (2016.01)
  *G01D 5/353* (2006.01)
  *G01D 11/24* (2006.01)
  *G02B 23/24* (2006.01)
  *G01B 11/00* (2006.01)
  *G01N 3/00* (2006.01)

(52) U.S. Cl.
  CPC ......... *G01D 11/24* (2013.01); *G02B 23/2476* (2013.01); *A61B 2034/2046* (2016.02); *A61B 2034/2061* (2016.02); *G01B 11/00* (2013.01); *G01N 3/00* (2013.01)

(56) References Cited

U.S. PATENT DOCUMENTS

| | | | | |
|---|---|---|---|---|
| 2012/0289843 A1* | 11/2012 | Chopra | ................ | A61B 1/0005 600/508 |
| 2015/0208947 A1* | 7/2015 | Tojo | ................... | G02B 23/2476 600/104 |
| 2015/0216392 A1* | 8/2015 | Tojo | ................... | A61B 1/00009 600/103 |
| 2015/0223670 A1* | 8/2015 | Fujita | ................. | A61B 1/00036 600/109 |

FOREIGN PATENT DOCUMENTS

| | | |
|---|---|---|
| JP | H06-154154 A | 6/1994 |
| JP | H11-19027 A | 1/1999 |
| JP | 2000-175861 A | 6/2000 |
| JP | 2006-288752 A | 10/2006 |
| JP | 2007-044412 A | 2/2007 |
| JP | 2014-076174 A | 5/2014 |
| JP | 2014-113352 A | 6/2014 |
| WO | WO 2008/059636 A1 | 5/2008 |

OTHER PUBLICATIONS

Japanese Office Action dated Mar. 19, 2019 in Japanese Patent Application No. 2016-564553.
German Office Action dated Jun. 12, 2018 in German Patent Application No. 11 2014 007 269.9.
Japanese Office Action dated Jun. 19, 2018 in Japanese Patent Application No. 2016-564554.
Chinese Office Action dated Mar. 9, 2018 in Chinese Patent Application No. 201480084173.4.
International Search Report dated Jan. 27, 2015 issued in PCT/JP2014/083747.

* cited by examiner

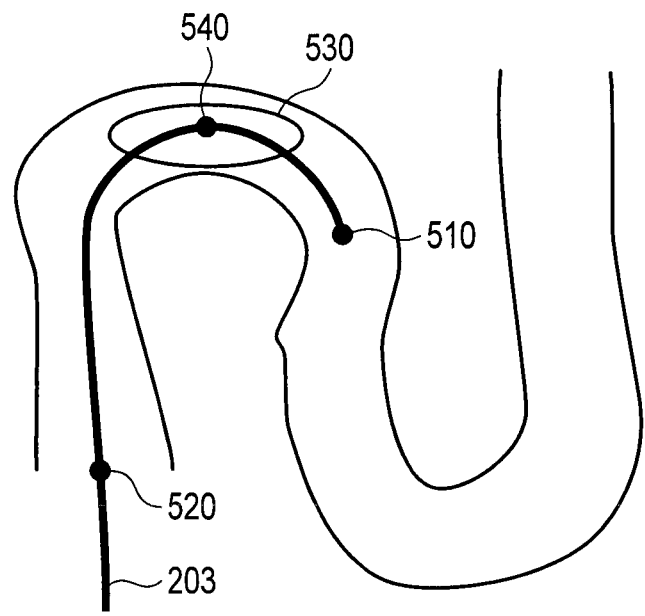
F I G. 8
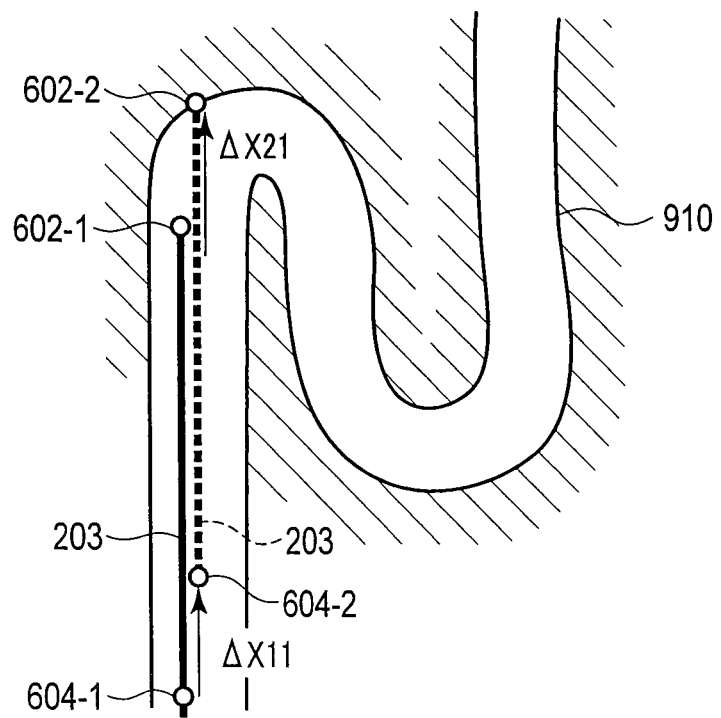
F I G. 9

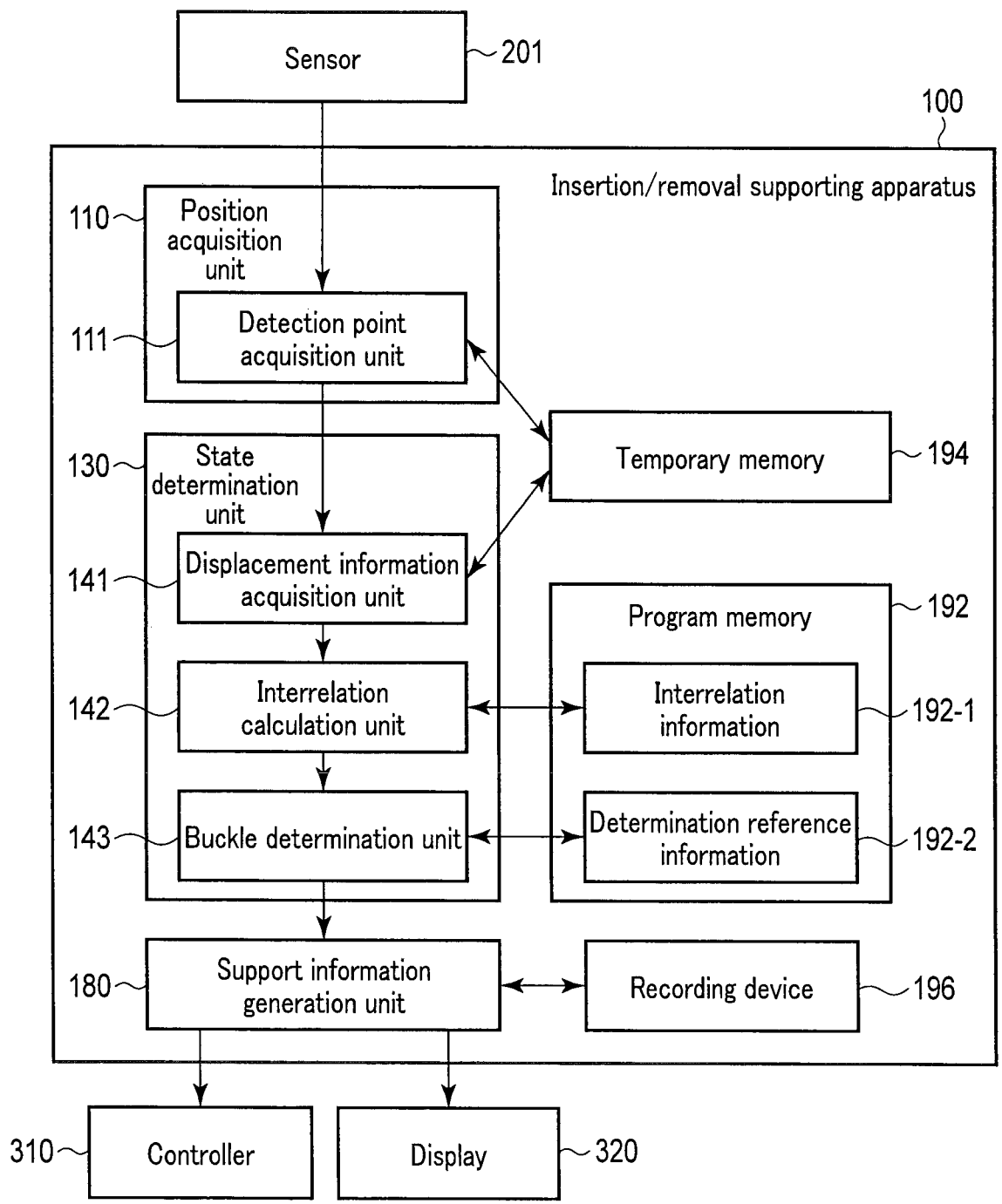
F I G. 12

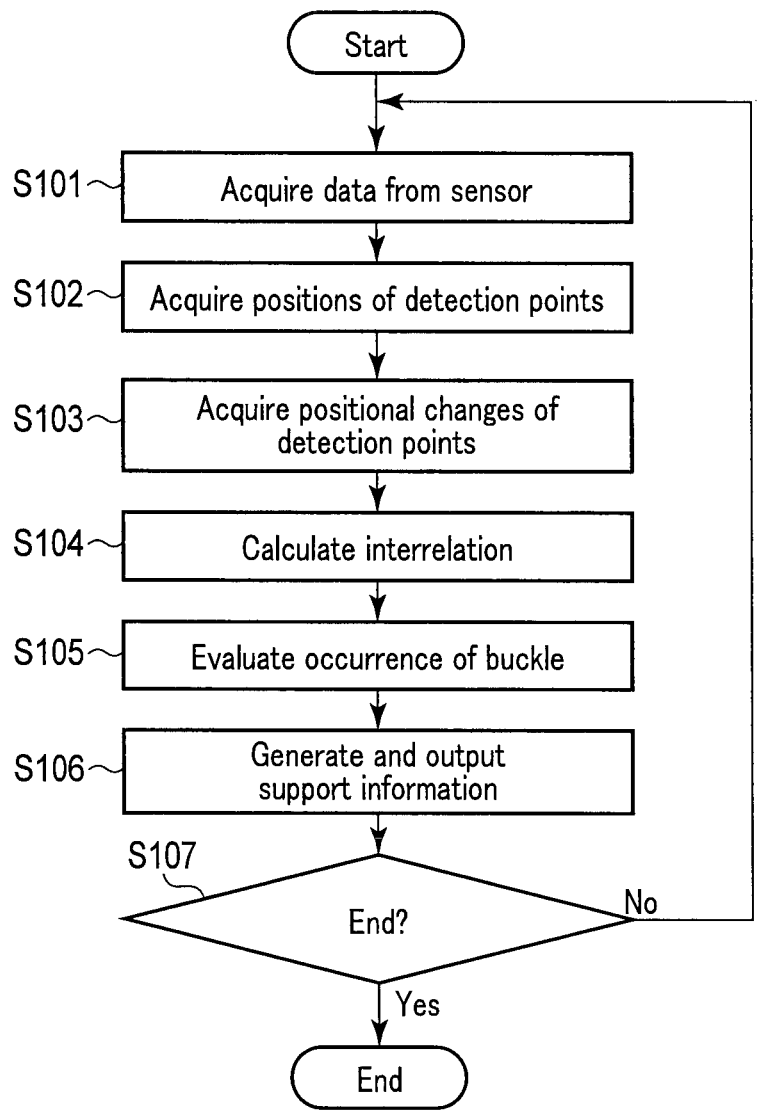
F I G. 13

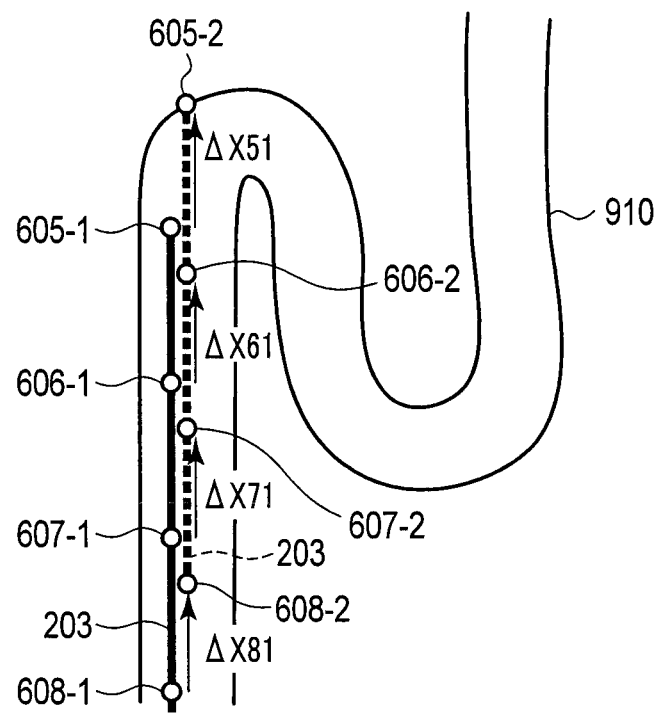
F I G. 14
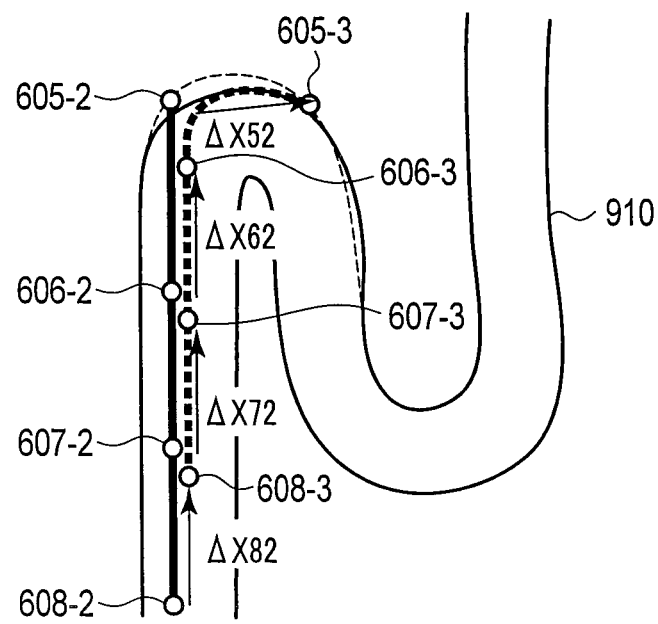
F I G. 15

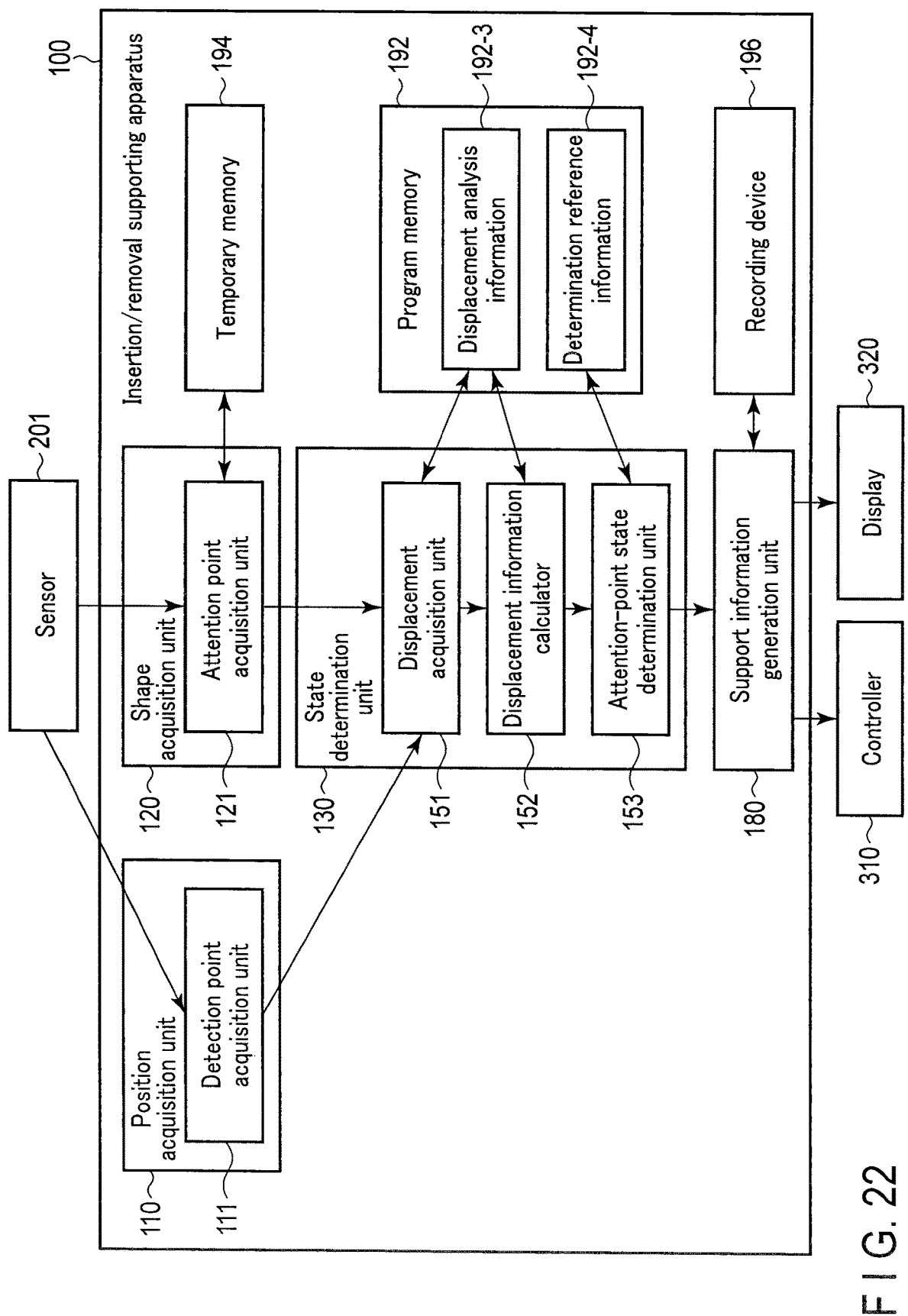
F I G. 22

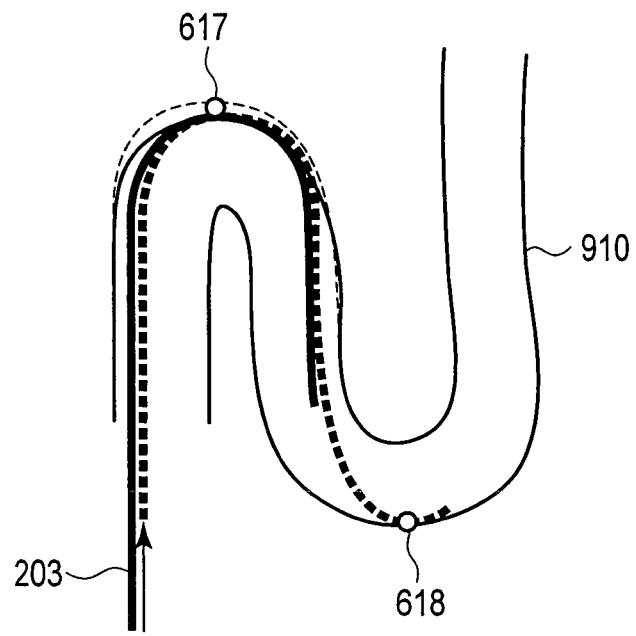
F I G. 24
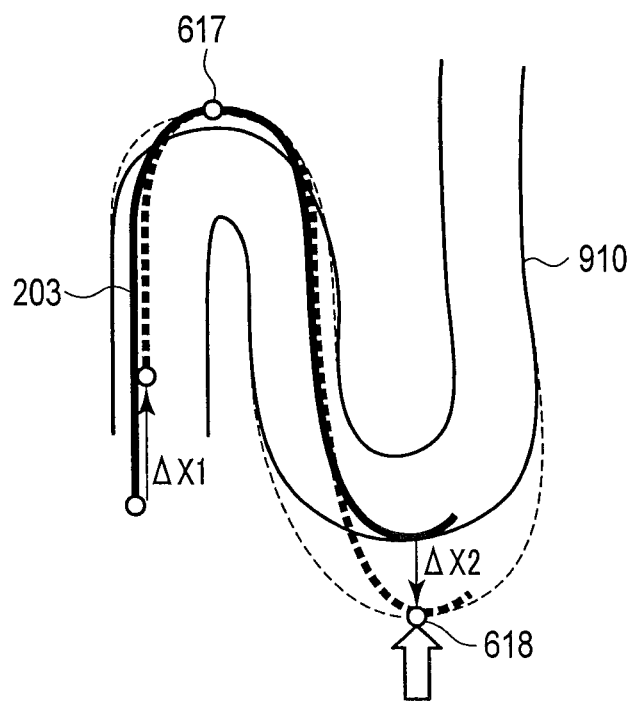
F I G. 25

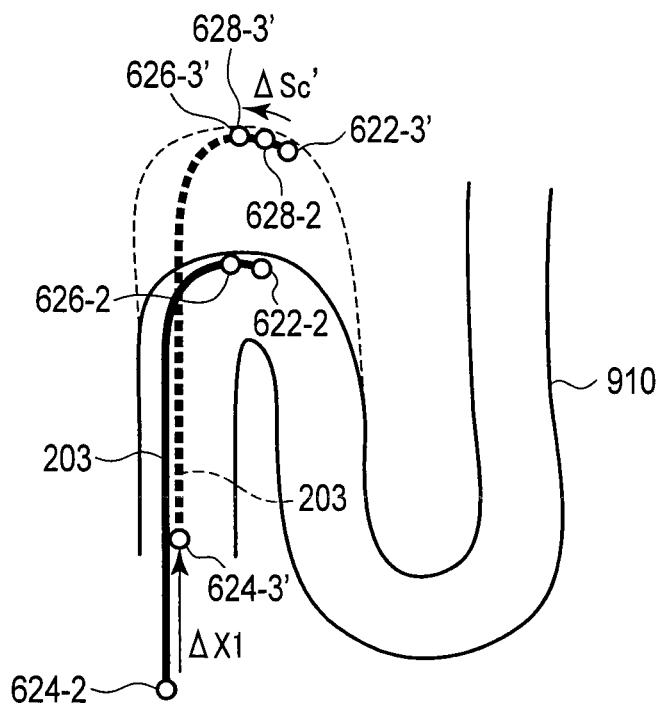
F I G. 28
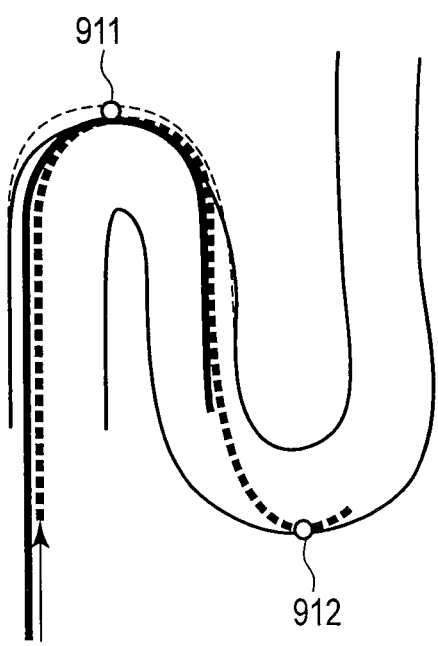
F I G. 29

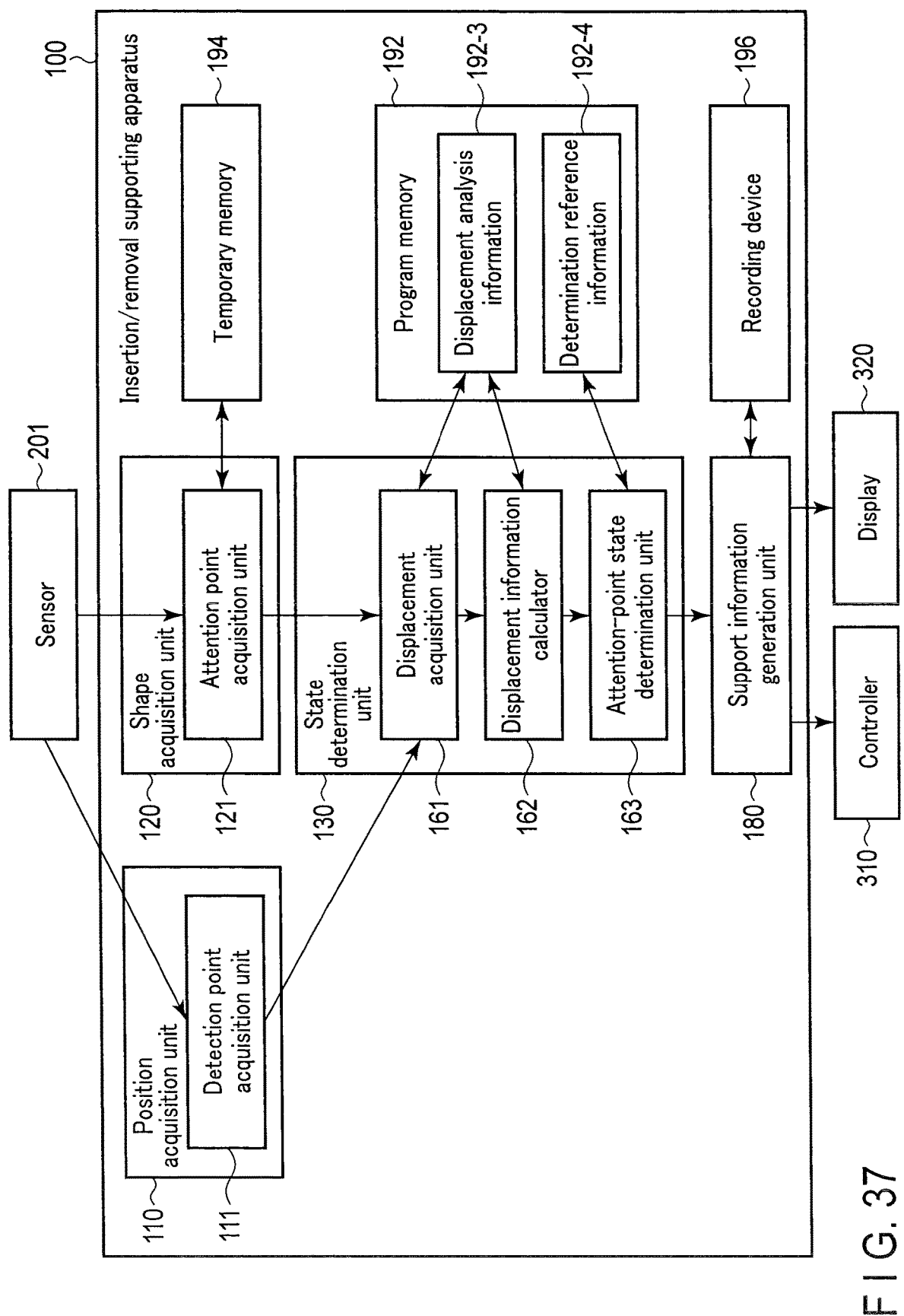
F I G. 37

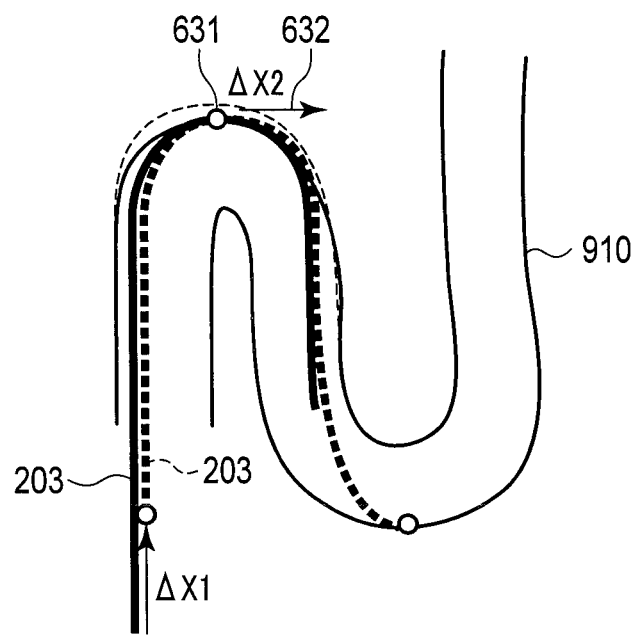
F I G. 39
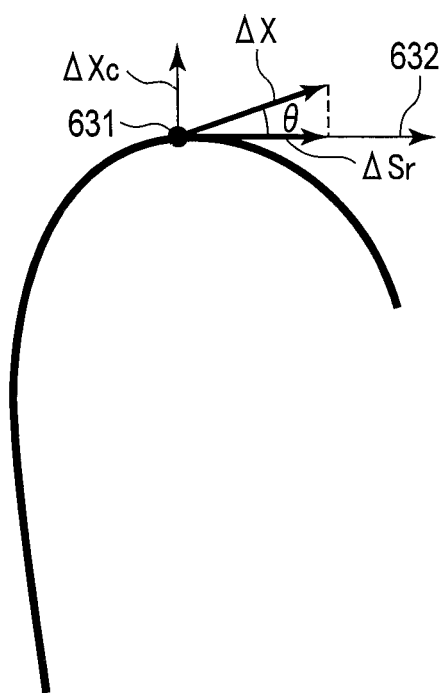
F I G. 40

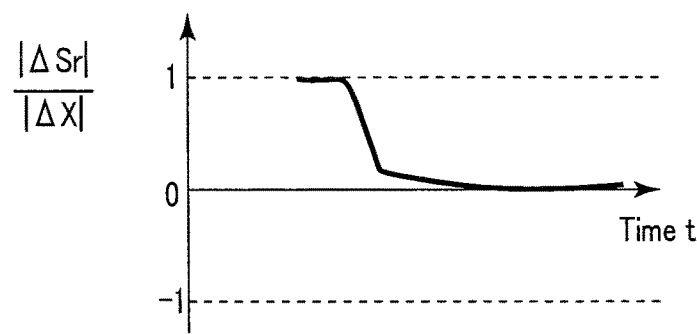
F I G. 41
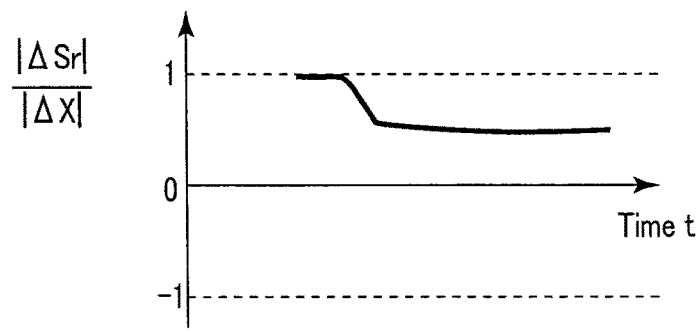
F I G. 42
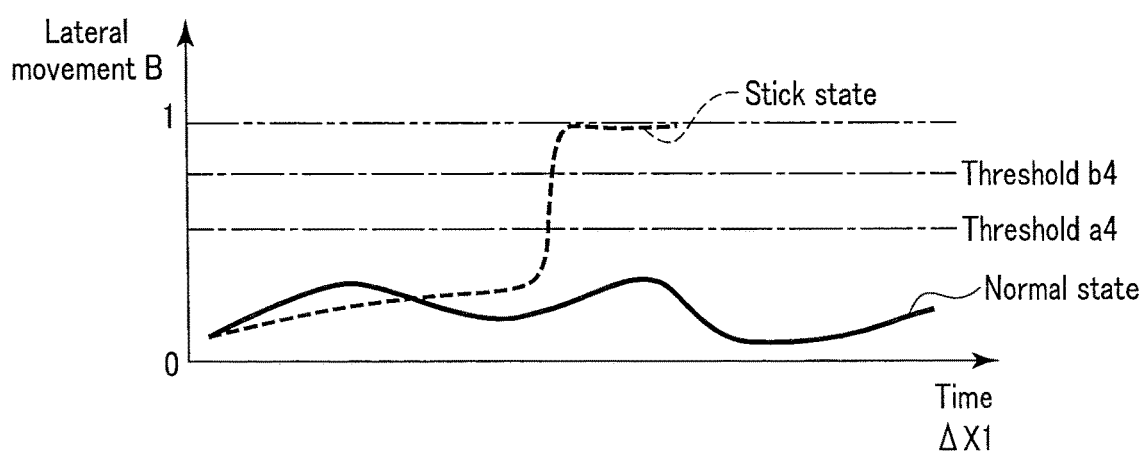
F I G. 43

INSERTION/REMOVAL SUPPORTING APPARATUS AND INSERTION/REMOVAL SUPPORTING METHOD

CROSS-REFERENCE TO RELATED APPLICATIONS

This application is a Continuation application of PCT Application No. PCT/JP2014/083747, filed Dec. 19, 2014, the entire contents of all of which are incorporated herein by references.

BACKGROUND OF THE INVENTION

1. Field of the Invention

The present invention relates to an insertion/removal supporting apparatus and an insertion/removal supporting method.

2. Description of the Related Art

An insertion/removal apparatus having an elongated insertion member, such as the insertion section of an endoscope, is generally known in the art. For example, when the insertion section of an endoscope is inserted into a subject, the user should preferably know the state of the insertion section. If the state of the insertion section is known, the user can easily insert the insertion section into the subject. Under the circumstances, a number of technologies for permitting the user to know the state of the insertion member of an insertion/removal apparatus are known in the art.

For example, Jpn. Pat. Appln. KOKAI Publication No. 2007-44412 discloses the following technology. According to the technology, an endoscope insertion shape detecting probe is provided in the insertion section of an endoscope. The endoscope insertion shape detecting probe includes detection light transmission means. The detection light transmission means is configured to change the optical loss amount in accordance with a bending angle. The use of such an endoscope insertion shape detecting probe enables detection of a bending angle of the insertion section of the endoscope. As a result, the bending shape of the insertion section of the endoscope can be reproduced.

For example, Jpn. Pat. Appln. KOKAI Publication No. 6-154153 discloses the following technology. According to the technology, a sensor support member is provided in the insertion section of an endoscope, and a distortion gauge is attached to the sensor support member. The use of the distortion gauge enables detection of an external force which is applied to the insertion section of the endoscope in a specific direction. As a result, information on the external force applied to the insertion section of the endoscope can be acquired.

For example, Jpn. Pat. Appln. KOKAI Publication No. 2000-175861 discloses the following technology. According to the technology, an endoscope system is provided with shape estimation means for estimating the shape of the insertion section of an endoscope. Based on how the shape estimation means estimates the shape of the insertion section of the endoscope, the endoscope system issues a warning, when required. For example, if the insertion section of the endoscope is detected as forming a loop, the user is warned to take notice of the state by display or sound.

There is a demand for an apparatus and a method which enable the user to know, in more detail, how the state of the insertion section of an insertion/removal apparatus is. There is also a demand for an apparatus and method which enable the user to know, in more detail, how the state of the subject is when the insertion section is inserted therein.

BRIEF SUMMARY OF THE INVENTION

According to an aspect of the present invention, supporting apparatus for supporting insertion of a flexible insertion member into a subject and removal thereof, comprising an attention point acquisition unit which specifies at least one first attention point specified by a shape of the insertion member, a first displacement acquisition unit which acquires a first displacement of the first attention point, and a determination unit which determines the state of the insertion member or the subject at a position corresponding to the first attention point, based on displacement information including information on the first displacement.

According to another aspect of the present invention, a supporting method for supporting insertion of a flexible insertion member into a subject and removal thereof, comprising specifying at least one attention point specified by a shape of the insertion member, acquiring a first displacement of the attention point; and determining how a state of the insertion member or the subject is at a position corresponding to the attention point, based on displacement information including information on the first displacement.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 8 is an explanatory diagram illustrating information obtained by a sensor according to one embodiment.

FIG. 9 illustrates a first state determination method and schematically illustrates how an insertion section is moved from time t1 to time t2.

FIG. 12 is a block diagram schematically illustrating an exemplary configuration of an insertion/removal supporting apparatus employed in the first state determination method.

FIG. 13 is a flowchart illustrating an example of processing performed in the first state determination method.

FIG. 14 illustrates a first variant of the first state determination method and schematically illustrates how an insertion section is moved from time t1 to time t2.

FIG. 15 illustrates the first variant of the first state determination method and schematically illustrates an example of how the insertion section is moved from time t2 to time t3.

FIG. 22 is a block diagram schematically illustrating an exemplary configuration of an insertion/removal supporting apparatus employed in the second state determination method.

FIG. 24 illustrates a variant of the second state determination method and schematically illustrates an example of how an insertion section is moved.

FIG. 25 illustrates the variant of the second state determination method and schematically illustrates an example of how the insertion section is moved.

FIG. 28 illustrates the third state determination method and schematically illustrates another example of how the insertion section is moved from time t2 to time t3.

FIG. 29 illustrates the third state determination method and schematically illustrates an example of how the insertion section is moved.

FIG. 37 is a block diagram schematically illustrating an exemplary configuration of an insertion/removal supporting apparatus employed in the third state determination method.

FIG. 39 illustrates a fourth state determination method and schematically illustrates an example of how an insertion section is moved.

FIG. 40 illustrates a relationship between tangential direction and an amount of movement in the fourth state determination method.

FIG. 41 illustrates an example of changes in the ratio of a tangential-direction in the displacement of an insertion section with time.

FIG. 42 illustrates another example of changes in the ratio of the tangential-direction in the displacement of the insertion section with time.

FIG. 43 illustrates an example of changes in lateral movement of an insertion section with time.

DETAILED DESCRIPTION OF THE INVENTION

Figure 1:
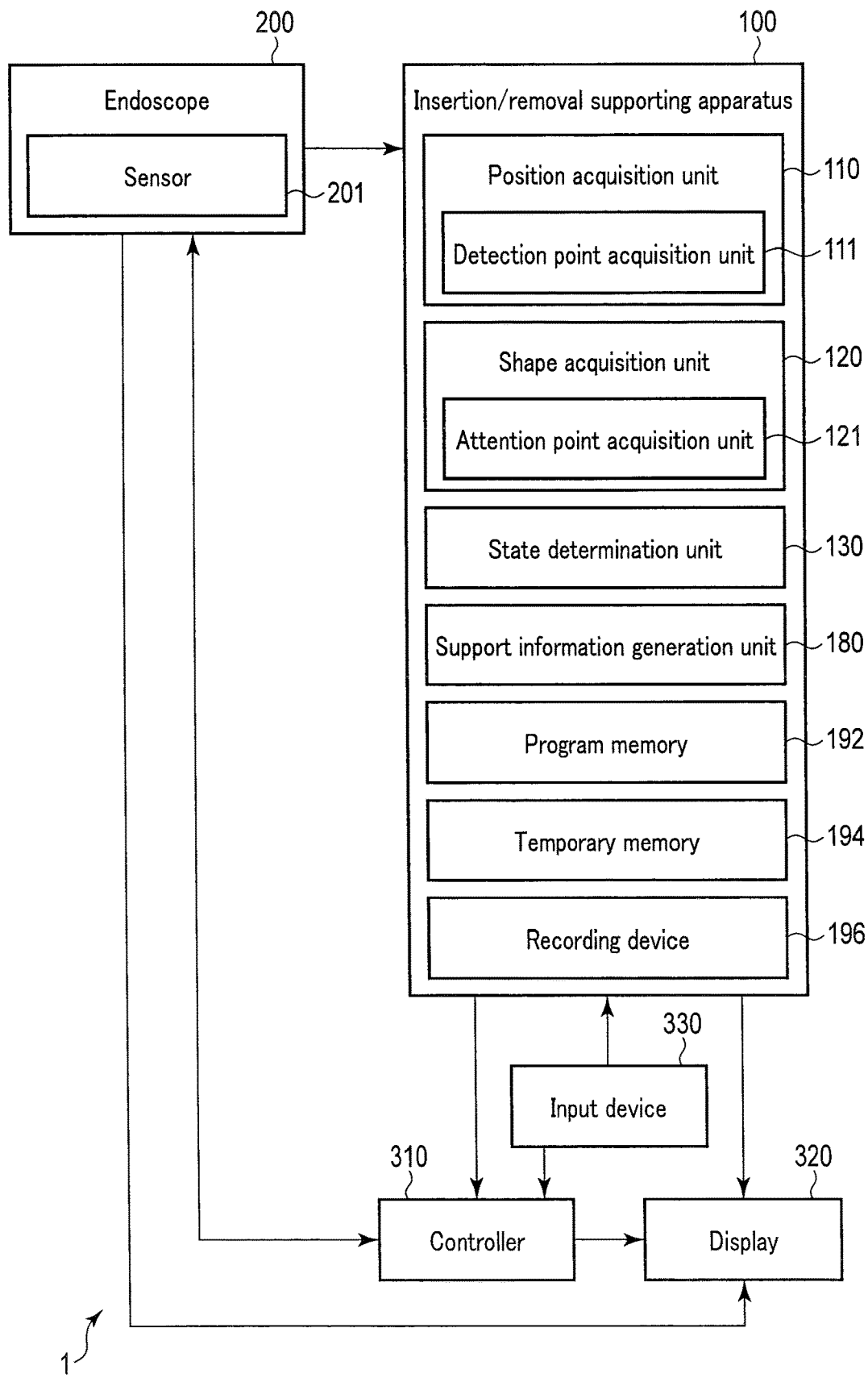
FIG. 1 schematically illustrates an exemplary configuration of an insertion/removal apparatus according to one embodiment.

One embodiment of the present invention will be described with reference to the accompanying drawings. FIG. 1 schematically illustrates an exemplary configuration of an insertion/removal apparatus 1 according to the embodiment. The insertion/removal apparatus 1 comprises an insertion/removal supporting apparatus 100, an endoscope 200, a controller 310, a display 320 and an input device 330.

The endoscope 200 is a general type of endoscope. The controller 310 controls the operation of the endoscope 200. The controller 310 may acquire information required for control from the endoscope 200. The display 320 is a general type of display. The display 320 includes, for example, a liquid crystal display. The display 320 is configured to show images acquired by the endoscope 200 and information created by the controller 310 and related to an operation of the endoscope 200. The input device 330 accepts user's inputs to be supplied to the insertion/removal supporting apparatus 100 and the controller 310. The input device 330 includes, for example, a button switch, a dial, a touch panel and a keyboard etc. The insertion/removal supporting apparatus 100 performs information processing for supporting the user's operation of inserting the insertion section of the endoscope 200 into a subject and removing the insertion section from the subject.

Figure 2:
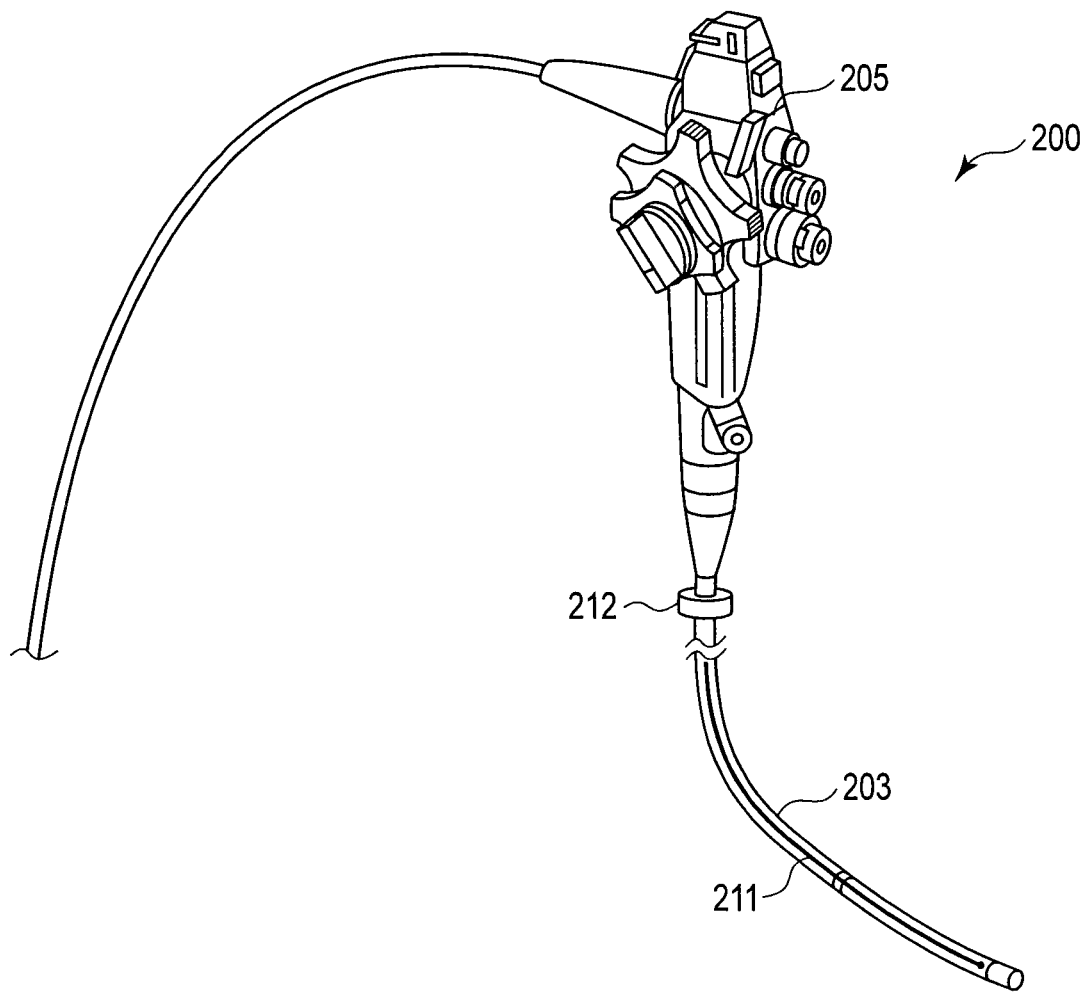
FIG. 2 illustrates an exemplary configuration of a sensor arranged at an endoscope according to one embodiment.
Figure 3:
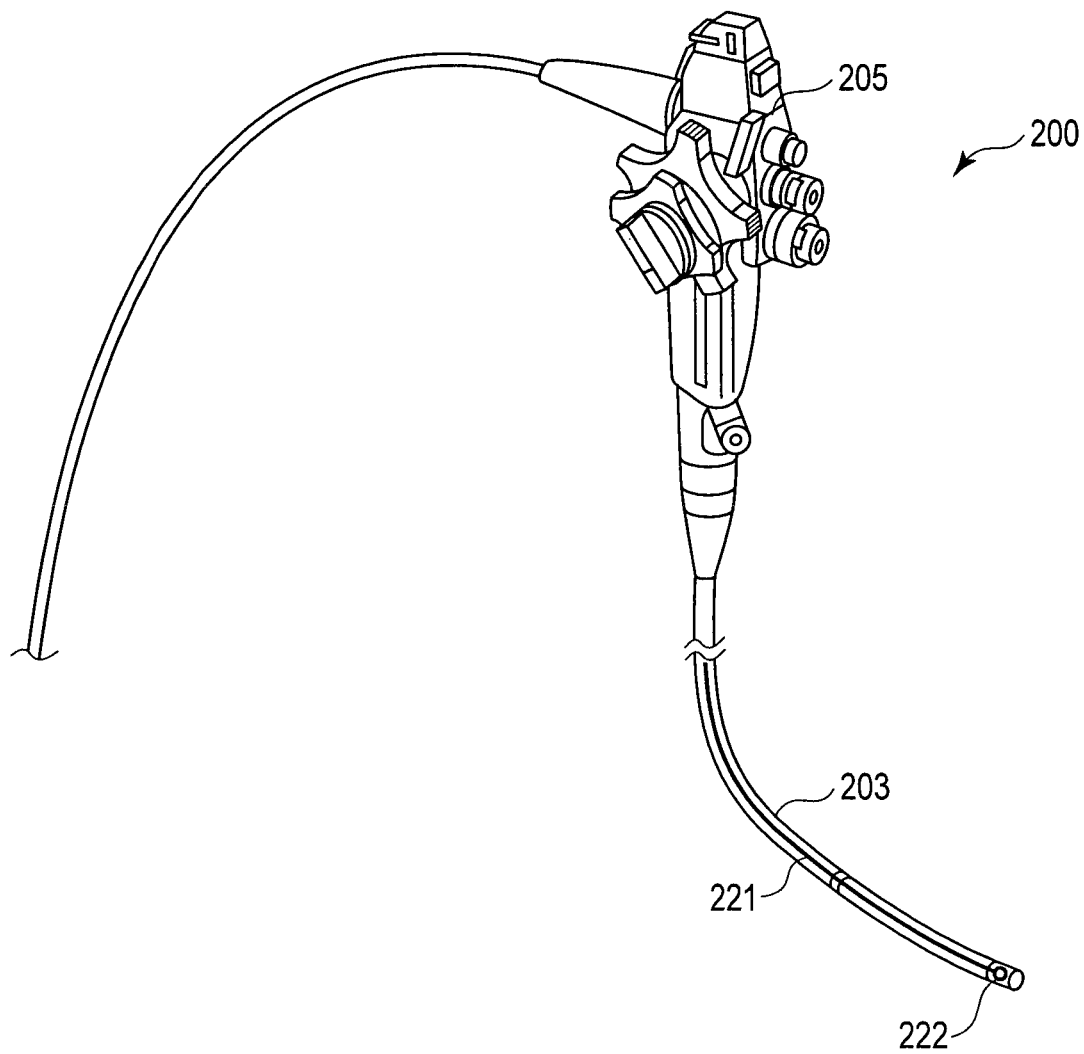
FIG. 3 illustrates an exemplary configuration of a sensor arranged at an endoscope according to one embodiment.
Figure 4:
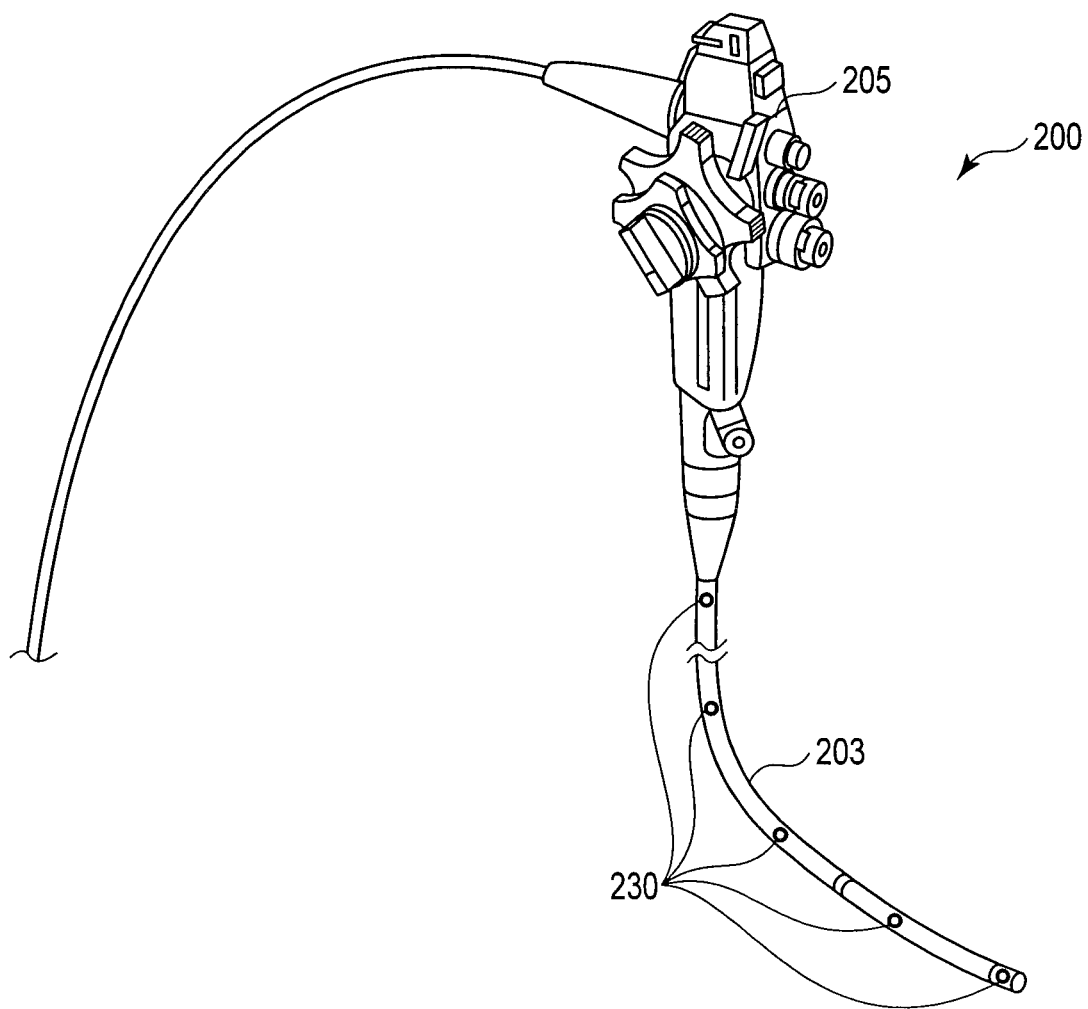
FIG. 4 illustrates an exemplary configuration of a sensor arranged at an endoscope according to one embodiment.

The endoscope 200 of the present embodiment is, for example, a large-intestine endoscope, that is colonoscope. As shown in FIGS. 2 to 4, the endoscope 200 comprises an insertion section 203, which is an elongated insertion member having flexibility, and an operation section 205 provided at an end of the insertion section 203. In the descriptions set forth below, that end of the insertion section 203 at which the operation section 205 is provided will be referred to as a rear end, and the other end of the insertion section 203 will be referred to as a distal end.

A camera is provided at the distal end of the insertion section 203, and images are acquired by the camera. After being subjected to general image processing, the acquired images are displayed on the display 320. A bending portion is provided at the distal end of the insertion section 203, and the bending portion is bent in response to an operation of the operation section 205. The user inserts the insertion section 203 into the subject, for example, by grasping the operation section 205 with his or her left hand and advancing or retreating the insertion section 203 with his or her right hand. In this type of endoscope 200, a sensor 201 is arranged at the insertion section 203 to acquire the position of each portion of the insertion section 203 and the shape of the insertion section 203.

The sensor 201 is one of various types of sensors. A configuration example of the sensor 201 will be described with reference to FIGS. 2 to 4.

FIG. 2 shows a first example of the configuration of the sensor 201. In the first example, the insertion section 203 is provided with a shape sensor 211 and an insertion amount sensor 212. The shape sensor 211 is a sensor for acquiring the shape of the insertion section 203. Based on an output of the shape sensor 211, the shape of the insertion section 203 can be acquired. The insertion amount sensor 212 is a sensor for acquiring an insertion amount by which the insertion section 203 is inserted into a subject. Based on an output of the insertion amount sensor 212, the position of a predetermined rear end portion of the insertion section 203 measured by the insertion amount sensor 212 can be acquired. The position at each portion of the insertion section 203 can be acquired based on both the position of the predetermined rear end portion of the insertion section 203 and the shape of the insertion section 203 including the predetermined rear end portion.

FIG. 3 shows a second example of the configuration of the sensor 201. In the second example, the insertion section 203 is provided with a shape sensor 221 for acquiring the shape of the insertion section 203, and a position sensor 222. The position sensor 222 detects the position of a portion where the position sensor 222 is arranged. FIG. 3 shows an example in which the position sensor 222 is at the distal end of the insertion section 203. The position, direction and curvature of each portion (any portion desired) of the insertion section 203 can be acquired by either calculation or estimation, based on the shape of the insertion section 203 acquired based on the output of the shape sensor 221 and the position acquired based on the output of the position sensor 222 and representing the portion where the position sensor 222 is provided.

FIG. 4 shows a third example of the configuration of the sensor 201. In the third example, the insertion section 203 is provided with a plurality of position sensors 230 for acquiring the respective positions of the insertion section 203. Based on outputs of the position sensors 230, positions of those portions where the position sensors 230 are provided in the insertion section 203 can be acquired. The shape of the insertion section 203 can be acquired by combination of information on the positions.

Figure 5:
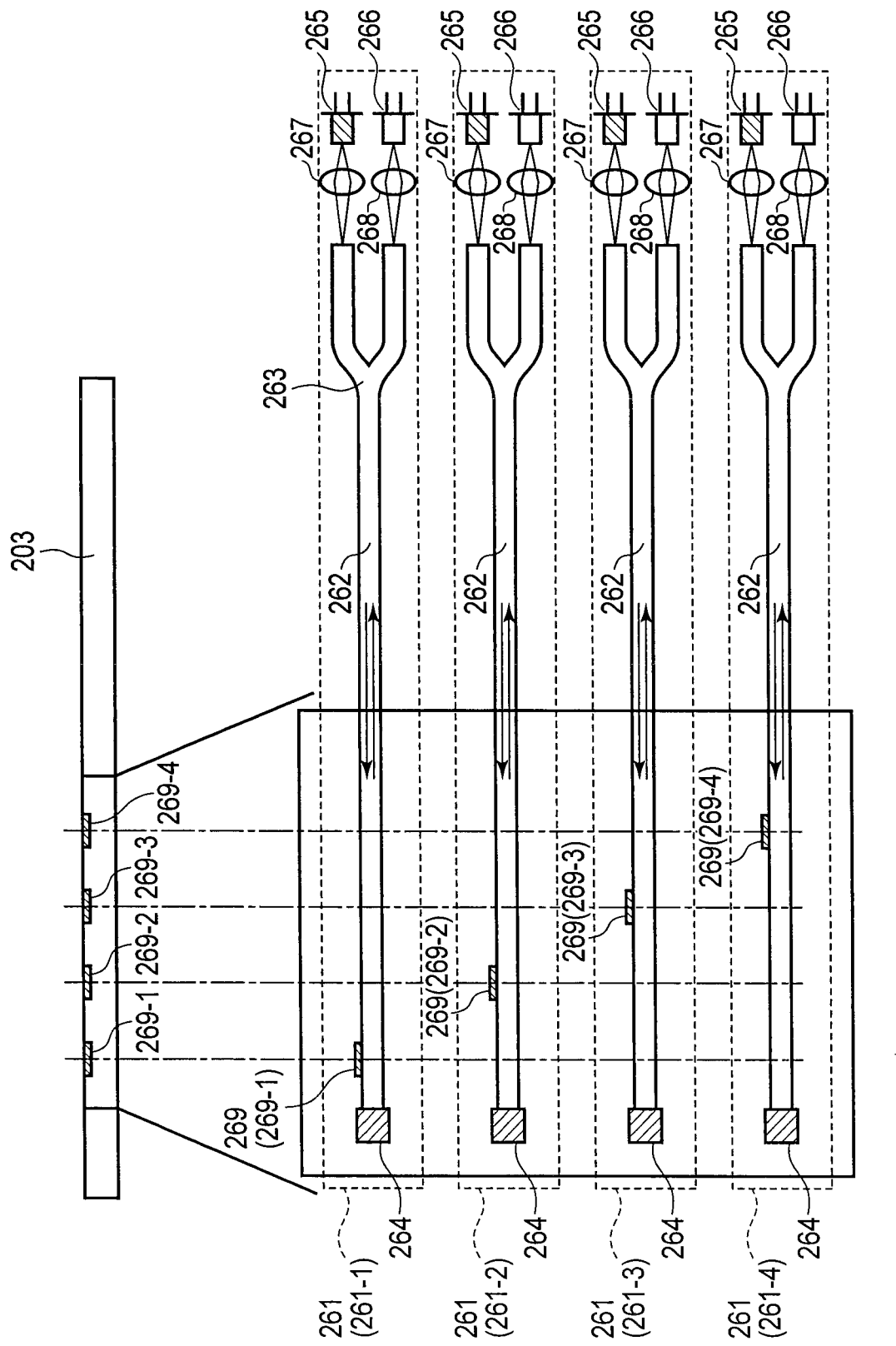
FIG. 5 schematically illustrates an exemplary configuration of a shape sensor according to one embodiment.

A configuration example of the shape sensor 211, 221 will be described with reference to FIG. 5. The shape sensor 260 provided in the insertion section 203 of this example includes a plurality of shape detectors 261. For the sake of simplicity, FIG. 5 shows a case where four shape detectors 261 are provided. To be more specific, the shape sensor 260 includes a first shape detector 261-1, a second shape detector 261-2, a third shape detector 261-3 and a fourth shape detector 261-4. The number of shape detectors may be any number.

Each shape detector 261 includes an optical fiber 262 extending along the insertion section 203. A reflector 264 is provided at the distal end of the optical fiber 262. A branching portion 263 is provided in the rear end portion of the optical fiber 262. A light-incidence lens 267 and a light source 265 are provided at the end of one branch portion of the rear end portion of the optical fiber 262. A light-emission lens 268 and a light detector 266 are provided at the end of the other branch portion of the rear end portion of the optical fiber 262. The optical fiber 262 is provided with a detection area 269. In this detection area 269, the first shape detector 261-1 is provided with a first detection area 269-1, the second shape detector 261-2 is provided with a second detection area 269-2, the third shape detector 261-3 is provided with a third detection area 269-3, and the fourth shape detector 261-4 is provided with a fourth detection area 269-4. These detection areas are arranged at positions different from each other in the longitudinal direction of the insertion section 203.

The light emitted from the light source 265 passes through the light-incidence lens 267 and is incident on the optical fiber 262. The light travels through the optical fiber 262 in the direction toward the distal end and is reflected by the reflector 264 provided at the distal end. The reflected light travels through the optical fiber 262 in the direction toward the rear end, passes through the light-emission lens 268, and is then incident on the light detector 266. The light propagation efficiency in the detection area 269 changes in accordance with the bending state of the detection area 269. Therefore, the bending state of the detection area 269 can be acquired based on the amount of light detected by the light detector 266.

More specifically, the bending state of the first detection area 269-1 can be acquired based on the amount of light detected by the light detector 266 of the first shape detector 261-1. Likewise, the bending state of the second detection area 269-2 can be acquired based on the amount of light detected by the light detector 266 of the second shape detector 261-2, the bending state of the third detection area 269-3 can be acquired based on the amount of light detected by the light detector 266 of the third shape detector 261-3, and the bending state of the fourth detection area 269-4 can be acquired based on the amount of light detected by the light detector 266 of the fourth shape detector 261-4. In this manner, the bending states of the respective portions of the insertion section 203 are detected, and the shape of the entire insertion section 203 can be acquired.

Next, a configuration example of the insertion amount sensor 212 will be described with reference to FIGS. 6 to 7.

Figure 6:
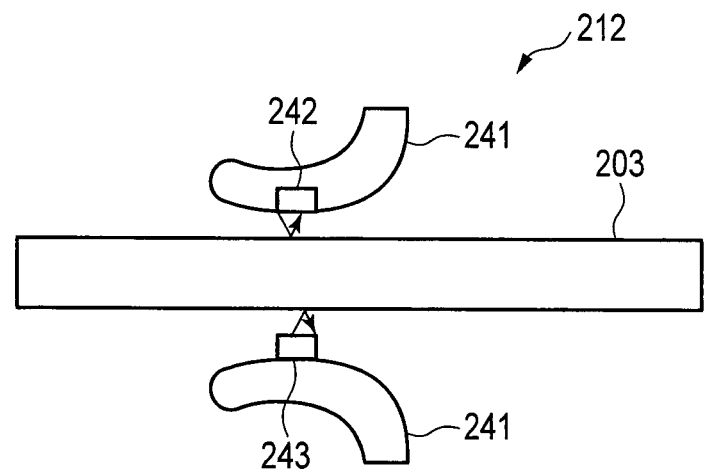
FIG. 6 schematically illustrates an exemplary configuration of an insertion amount sensor according to one embodiment.

FIG. 6 shows an example of the configuration of the insertion amount sensor 212. In this example, the insertion amount sensor 212 includes a holder 241 to be fixed at the insertion port of the subject. A first encoder head 242 for detection in the insertion direction and a second encoder head 243 for detection in the twisting direction are provided on the holder 241. An encoder pattern is formed on the insertion section 203. The first encoder head 242 detects an insertion amount of the insertion section 203 in the longitudinal direction when the insertion section 203 is inserted, based on the encoder pattern formed on the insertion section 203. The second encoder head 243 detects a rotation amount of the insertion section 203 in the circumferential direction when the insertion section 203 is inserted, based on the encoder pattern formed on the insertion section 203.

Figure 7:
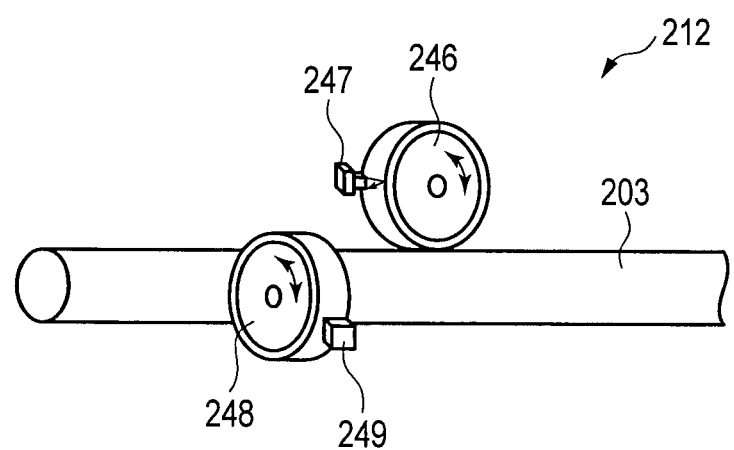
FIG. 7 schematically illustrates an exemplary configuration of an insertion amount sensor according to one embodiment.

FIG. 7 shows another example of the configuration of the insertion amount sensor 212. In this example, the insertion amount sensor 212 includes a first roller 246 for detection in the insertion direction, a first encoder head 247 for detection in the insertion direction, a second roller 248 for detection in the twisting direction, and a second encoder head 249 for detection in the twisting direction. When the insertion section 203 moves in the longitudinal direction, the first roller 246 rotates in accordance with the movement. An encoder pattern is formed on the first roller 246. A first encoder head 247 is opposed to the first roller 246. The first encoder head 247 detects an insertion amount of the insertion section 203 in the longitudinal direction when the insertion section 203 is inserted, based on how the first roller 246 is rotated by the insertion. When the insertion section 203 rotates in the circumferential direction, the second roller 248 rotates in accordance with the rotation. An encoder pattern is formed on the second roller 248. A second encoder head 249 is opposed to the second roller 248. The second encoder head 249 detects a rotation amount of the insertion section 203 in the circumferential direction when the insertion section 203 is inserted, based on how the second roller 248 is rotated by the rotation.

The insertion amount sensors 212 shown in FIGS. 6 and 7 use a position of the insertion amount sensors 212 as a reference position and specify which portion of the insertion section 203 is located and also specify the rotating angle of that portion. That is, the position of a discretional portion of the insertion section 203 can be specified.

Next, a description will be given of the position sensors 222 and 230. Each of the position sensors 222 and 230 includes a coil provided in the insertion section 203 and configured to generate a magnetic field, and a receiver provided outside the subject. The position of each coil can be acquired by detecting the magnetic field generated by the magnetic coil with receiver. The position sensors are not limited to sensors utilizing magnetic fields; they may be configured in a number of ways. Each position sensor may be made by a transmitter provided on the insertion section 203 and configured to emit a light wave, a sound wave, an electromagnetic wave or the like, and a receiver provided outside the subject and configured to receive the signal emitted from the transmitter.

Accordingly, information as described below can be obtained based on outputs of the sensor 201 including the shape sensor, insertion amount sensor, position sensor and a combination thereof. The information that can be obtained will be described with reference to FIG. 8. The sensor 201 enables acquisition of the position of the insertion section 203, for example, of the distal end 510 of the insertion section 203. The position of the distal end 510, for example, can be expressed as coordinates using the insertion port of the subject as a reference.

For example, in the first example in which the shape sensor 211 and the insertion amount sensor 212 are provided, as shown in FIG. 2, the position of that portion of the insertion section 203 which is located at the insertion port of the subject is acquired. With this position as a reference and based on the shape of the insertion section 203 acquired by the shape sensor 211, the position of the distal end 510 of the insertion section 203 can be acquired relative to the insertion port of the subject.

For example, in the second example in which the shape sensor 221 and the position sensor 222 are provided, as shown in FIG. 3, the position at which the position sensor 222 is provided in the insertion section 203 is known. With this position as a reference and based on the shape of the insertion section 203 acquired by the shape sensor 221, the position of the distal end 510 of the insertion section 203 can be acquired relative to the position sensor 222. Since the position of the position sensor 222 relative to the subject can be acquired based on an output of the position sensor 222, the position of the distal end 510 of the insertion section 203 relative to the insertion port of the subject can be acquired. Where the position sensor 222 is located at the distal end 510 of the insertion section 203, the position of the distal end 510 of the insertion section 203 relative to the insertion port of the subject can be directly acquired based on an output of the position sensor 222.

For example, in the third example in which the position sensor 230 is provided, as shown in FIG. 4, the position of the distal end 510 of the insertion section 203 relative to the insertion port of the subject can be acquired based on an output from the position sensor 230 provided near the distal end of the insertion section 203.

Like the position of the distal end 510 of the insertion section 203, the position of any portion 520 of the insertion section 203 relative to the insertion port of the subject can be acquired. In the above, the insertion port of the subject is described as a reference position, but this is not restrictive. The reference position may be any position desired. A point on the insertion section 203 which is (directly) sensed will be referred to as a "detection point." In the present embodiment, the point on the insertion section 203 from which position information is (directly) acquired will be referred to as a "detection point."

Based on an output of the sensor 201, the shape of the insertion section 203 can be acquired. For example, where the shape sensors 211 and 221 are provided as in the first and second examples mentioned above, the shape of the insertion section 203 can be acquired based on outputs of those sensors. Where a plurality of position sensors 230 are provided as in the third example, the shape of the insertion section 203 can be obtained based on the information detected by the position sensors 230 and relating to the positions where the position sensors 230 are arranged, and operation results for interpolating the positions between the position sensors 230.

Where the shape of the insertion section 203 is determined, the positions of the characteristic portions of the insertion section 203 can be obtained. For example, where a bending portion is regarded as a predetermined shape area 530, the position corresponding to the turn-around point 540 of the bending portion of the insertion section 203 can be obtained. The turn-around point is determined, for example, as follows. In the example shown in FIG. 8, the insertion section 203 is first moved upward, as viewed in the drawing, is then bent, and is then moved downward. The turn-around point is defined as a point located uppermost in FIG. 8. Where the insertion section 203 is bent, the turn-around point can be defined as an endmost point in a predetermined direction. That point on the insertion section 203 from which sensing information is to be obtained directly or by estimation will be referred to as an "attention point." In the present embodiment, the "attention point" is a characteristic point determined based on the shape of the insertion section 203. The attention point need not be the turn-around point described above but may be any point as long as it is a characteristic point determined based on the shape of the insertion section 203.

In order to acquire the above-mentioned information based on outputs of the sensor 201, the insertion/removal supporting apparatus 100 in the present embodiment comprises a position acquisition unit 110 and a shape acquisition unit 120, as shown in FIG. 1. The position acquisition unit 110 performs processing for the position information on the respective portions of the insertion section 203. The position acquisition unit 110 includes a detection position acquisition unit 111. The detection point acquisition unit 111 specifies the position of a detection point. The position acquisition unit 110 can specify not only the position of the detection point but also a position of an attention point, which is any point of the insertion section 203 and can be determined based on an output of the sensor 201. The shape acquisition unit 120 performs processing for the information on the shape of the insertion section 203. The shape acquisition unit 120 includes an attention point acquisition unit 121. Based on the shape of the insertion section 203 and the position information calculated by the position acquisition unit 110, the attention point acquisition unit 121 specifies the position of the attention point that can be obtained based on the shape.

The insertion/removal supporting apparatus 100 comprises a state determination unit 130. By utilizing the information representing the position of the detection point and the position of the attention point, the state determination unit 130 calculates a state of the insertion section 203 or a state of the subject into which the insertion section 203 is inserted. More specifically, as described later, it evaluates in a variety of ways whether the insertion section 203 moves in accordance with a shape of the insertion section 203, namely whether the insertion section 203 has self-following property. Based on the results of evaluation, it calculates a state of the insertion section 203 or a state of the subject into which the insertion section 203 is inserted.

The insertion/removal supporting apparatus 100 further comprises a support information generation unit 180. Based on the information calculated by the state determination unit 130 and representing the state of the insertion section 203 or the state of the subject, the support information generation unit 180 generates support information which supports the user when the user inserts the insertion section 203 into the subject. The support information generated by the support information generation unit 180 is expressed in words and figures, and these are displayed on a display 320. Based on the information calculated by the state determination unit 130 and representing the state of the insertion section 203 or the subject, the support information generation unit 180 generates various information which the controller 310 uses for controlling the operation of the endoscope 200.

The insertion/removal supporting apparatus 100 further comprises a program memory 192 and a temporary memory 194. The program memory 192 stores a program needed for an operation of the insertion/removal supporting apparatus 100, predetermined parameters, etc. The temporary memory 194 temporarily stores data generated by the respective units or sections of the insertion/removal supporting apparatus 100.

The insertion/removal supporting apparatus 100 further comprises a recording device 196. The recording device 196 stores support information generated by the support information generation unit 180. The recording device 196 need not be provided inside the insertion/removal supporting apparatus 100; it may be provided outside the insertion/removal supporting apparatus 100. Where the support information is stored in the recording device 196, the following advantages are obtained. That is, it allows later reproduction or analysis of the information representing the state of the insertion section 203 or the state of the subject based on the support information stored in the recording device 196. The information stored in the recording device 196 is used as reference information or history information when the insertion section 203 is inserted into the same subject.

For example, the position acquisition unit 110, the shape acquisition unit 120, the state determination unit 130, and the support information generation unit 180 or the like include a circuit/circuits such as a Central Processing Unit (CPU), an Application Specific Integrated Circuit (ASIC) or the like.

Next, a description will now be given as to how the information representing the state of the insertion section 203 or the subject is calculated.

[First State Determination Method]

In the first state determination method, the state of the insertion section 203 is determined based on the positional relations among a plurality of detection points.

FIG. 9 schematically illustrates how the insertion section 203 is moved from time t1 to time t2. The state of the insertion section 203 at time t1 is indicated by the thick solid line, while the state of the insertion section 203 at time t2 is indicated by the broken line. In the example shown in here, discretionary points in the distal end and the rear end portion of the insertion section 203 are specified as attention points. The discretionary portion on the rear end portion is regarded as a predetermined portion and will be referred to as a rear-side attention point. It is assumed here that the position where the position sensor is arranged is the rear-side attention point. In other words, a description will be given, referring to the case where the rear-side attention point is a detection point. This point will be hereinafter referred to as a rear-side detection point. One of the attention points is not limited to be at the distal end, it may be any point of the distal end portion, but the following description will be given on the assumption that the distal end is an attention point. In the description below, reference will be made to the case where the position sensor is arranged at the distal end portion. In other words, a description will be given of the case where the distal end portion is a detection point.

At time t1, the distal end of the insertion section 203 is located at a first distal end position 602-1. At time t1, the rear-side detection point of the insertion section 203 is located at a first rear end position 604-1. At time t2 which is after time t1 by $\Delta t$, the distal end of the insertion section 203 is located at a second distal end position 602-2. At time t2, the rear-side detection point of the insertion section 203 is located at a second rear end position 604-2.

Let us assume that the displacement from the first distal end position 602-1 to the second distal end position 602-2, namely the positional change of the distal end, is $\Delta X21$. Let us also assume that the displacement from the first rear end position 604-1 to the second rear end position 604-2, namely the positional change of the rear-side detection point, is $\Delta X11$. Where the insertion section 203 is inserted along the subject, as shown in FIG. 9, $|\Delta X21| \approx |\Delta X11|$ will be given.

Figure 10:
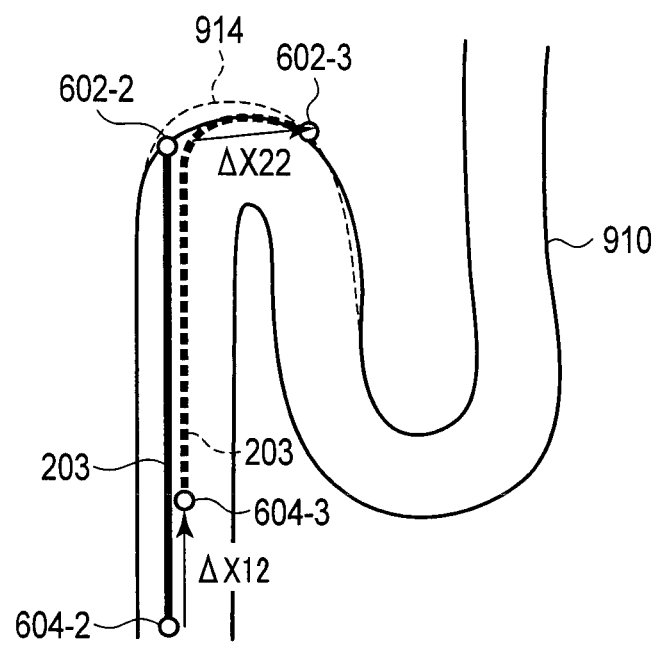
FIG. 10 illustrates the first state determination method and schematically illustrates an example of how the insertion section is moved from time t2 to time t3.

FIG. 10 is a schematic diagram illustrating a case where the insertion section 203 is inserted along the subject 910 in a flexure 914 of the subject. At time t3 which is after time t2 by $\Delta t$, the distal end of the insertion section 203 is located at a third distal end position 602-3. At time t3, the rear-side detection point of the insertion section 203 is located at a third rear end position 604-3. Let us assume that the displacement from the second distal end position 602-2 to the third distal end position 602-3, namely the positional change of the distal end, is X22. Let us also assume that the displacement from the second rear end position 604-2 to the third rear end position 604-3, namely the positional change of the rear-side detection point, is ΔX12. Where the insertion section 203 is inserted along the subject, as shown in FIG. 10, |ΔX22|≈|ΔX12| will be given.

Figure 11:
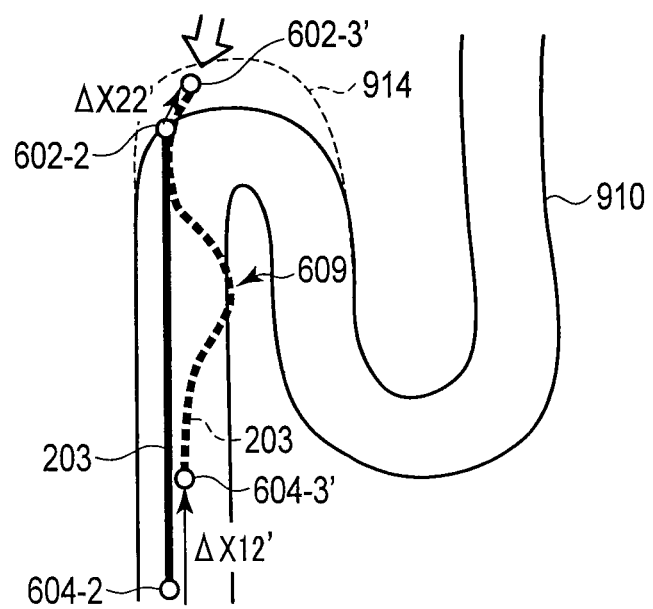
FIG. 11 illustrates the first state determination method and schematically illustrates another example of how the insertion section is moved from time t2 to time t3.

FIG. 11 is a schematic diagram illustrating a case where the insertion section 203 is not inserted along the subject 910 in the flexure 914 of the subject. At time t3 which is after time t2 by Δt, the distal end of the insertion section 203 is located at a third distal end position 602-3'. At time t3, the rear-side detection point of the insertion section 203 is located at a third rear end position 604-3'. Let us assume that the displacement from the second distal end position 602-2 to the third distal end position 602-3', namely the positional change of the distal end, is ΔX22'. Let us also assume that the displacement from the second rear end position 604-2 to the third rear end position 604-3', namely the positional change of the rear-side detection point, is ΔX12'. Where the insertion section 203 is not inserted along the subject, as shown in FIG. 11, |ΔX22'|≠|ΔX12'|(|ΔX22'|<|ΔX12'|) will be given.

In FIGS. 9 to 11 in this example, both the time period from time t1 to time t2 and the time period from time t2 to time t3 are equal values it, as is often the case with automatic measurement, but they may be different from each other. This holds true of the examples explained below.

In the case shown in FIG. 11, the distal end of the insertion section 203 is pushed or pressed by the subject 910, as indicated by the outlined arrow. Conversely, a degree of push of the subject 910 by the insertion section 203 increases at the distal end of the insertion section 203. In the case shown in FIG. 11, the insertion section 203 is buckled at the portion 609 between the distal end of the insertion section 203 and the rear-side detection point thereof.

When the amount of movement of the rear-side detection point which is a detection point on the rear end portion of the insertion section 203 is equal to the amount of movement of the distal end which is a detection point on the distal end portion of the insertion section 203, namely, when a degree of interrelation between the amount of movement of the rear-side detection point and the amount of movement of the distal end is high, it can be presumed that the insertion section 203 is smoothly inserted along the subject 910. When the amount of movement of the distal end is shorter than the amount of movement of the rear-side detection point, namely, when the degree of interrelation between the amount of movement of the rear-side detection point and the amount of movement of the distal end is low, it can be presumed that the distal end of the insertion section 203 does not smoothly move or gets stuck. In such a case, an unintended situation or abnormality may be occurring between the distal end and the rear-side detection point. As can be seen from the above, the buckle of the insertion section 203 and a level of pressing applied to the subject can be found based on analysis of the positional relations between the detection points obtained in the first state determination method. That is, the first state determination method enables acquisition of information representing the state of the insertion section or the state of the subject.

Let us assume that first operation support information α1 is introduced as a value representing the state of the insertion section 203 described above. The first operation support information α1 is defined as follows:

$$\alpha1 \equiv |\Delta X2|/|\Delta X1|$$

where ΔX2 is a displacement of the distal end and ΔX1 is a displacement of the rear-side detection point. The first operation support information α1 indicates that the closer to 1 the value of the first operation support information α1 is, the more properly the insertion section 203 is inserted along the subject 910.

The first operation support information α1 may be defined as follows:

$$\alpha1 \equiv (|\Delta X2|+C2)^L/(|\Delta X1|+C1)^M$$

where C1, C2, L and M are any real numbers.

By way of example, assuming that the detection noise component levels of ΔX1 and ΔX2 are N1 and N2 (N1, N2≥0), parameters C1, C2, L and M are defined as follows:

$$\begin{aligned}
C1 &= N1 & |\Delta X1| &\geq N1 \\
C2 &= -N2 & |\Delta X2| &\geq N2 \\
&= -|\Delta X2| & |\Delta X2| &< N2 \\
L &= M = 1
\end{aligned}$$

As N1 and N2, values which are approximately three times as large as the standard deviations (σ) of noise levels may be set.

In the measure against noise, C1 is positive and C2 is negative, as above, and by taking such a measure, the first operation support information α1 is obtained which reduces the adverse effects by the detection noise and lessens the detection errors caused by the detection noise. The way for reducing the adverse effects of noise can be applied to the calculation of other support information described later.

Where the endoscope 200 is a large-intestine endoscope, that is colonoscope, and the subject 910 is the large intestine, the flexure 914 mentioned above corresponds to the top portion of sigmoid colon (so-called "S-top").

FIG. 12 schematically illustrates a configuration example of the insertion/removal supporting apparatus 100 which can be employed for implementing the first state determination method.

The insertion/removal supporting apparatus 100 comprises a position acquisition unit 110 including a detection point acquisition unit 111, a state determination unit 130, and a support information generation unit 180. The detection point acquisition unit 111 acquires the positions of a plurality of detection points, based on information output from the sensor 201.

The state determination unit 130 includes a displacement information acquisition unit 141, an interrelation calculation unit 142, and a buckle determination unit 143. The displacement information acquisition unit 141 calculates displacements of detection points, based on how the positions of the detection points change with time. The interrelation calculation unit 142 calculates a degree of interrelation of the detection points, based on the displacements of the detection points and the interrelation information 192-1 stored in the program memory 192. The interrelation information 192-1 includes, for example, a relationship between the difference between the displacements of the detection points and an evaluation value of the degree of interrelation. The buckle determination unit 143 determines a buckle state of the insertion section 203, based on the calculated interrelation and determination reference information 192-2 stored in the program memory 192. The determination reference information 192-2 includes, for example, the relationship between the degree of interrelation and the buckle state.

The support information generation unit 180 generates operation support information, based on the determined buckle state. The operation support information is fed back to the control of the controller 310, is displayed on the display 320, or is stored in the recording device 196.

How the insertion/removal supporting apparatus 100 operates in the first state determination method will be described with reference to the flowchart shown in FIG. 13.

In step S101, the insertion/removal supporting apparatus 100 acquires output data from the sensor 201. In step S102, the insertion/removal supporting apparatus 100 acquires positions of detection points, based on the data acquired in step S101.

In step S103, the insertion/removal supporting apparatus 100 acquires how the position of each detection point changes with time. In step S104, the insertion/removal supporting apparatus 100 evaluates differences between change amounts of positions of each detection point. That is, it calculates the degree of interrelation of the variation in position of the respective detection points. In step S105, the insertion/removal supporting apparatus 100 perform evaluation of buckle such as whether a buckle occurs between the detection points and, if the buckle occurs, evaluates the state of the buckle, based on the degree of interrelation calculated in step S104.

In step S106, the insertion/removal supporting apparatus 100 generates proper support information to be used in later processing, based on the evaluation result representing whether the buckle occurs, and outputs the support information, for example, to the controller 310 and the display 320.

In step S107, the insertion/removal supporting apparatus 100 determines whether a termination signal for terminating the processing is entered. Unless the termination signal is entered, the processing returns to step S101. That is, the processing mentioned above is repeated until the termination signal is entered, and operation support information is output. If the termination signal is entered, the processing is brought to an end.

The use of the first state determination method enables positions of two or more detection points to be specified, and operation support information representing whether the abnormality (e.g., a buckled state of the insertion section 203) is occurred or not is generated (e.g.) based on the degree of interrelation of the amount of movements of the detection points.

In the above example, it is shown that the operation support information is generated by directly sensing the positions of the detection points. However, the present invention is not limited to this. The operation support information may be generated using information on attention points, namely any points of the insertion section 203. Where the positions of attention points are used, the positions of the attention points are acquired not by the detection point acquisition unit 111 but by the position acquisition unit 110, and the positions of the acquired attention points are used. In the other respects, the processing is similar to that described above.

[First Variant]

In the above example, it is shown that the number of detection points is two. However, this is not restrictive, and the number of detection points may be any number desired. If the number of detection points is large, it allows acquiring detailed information on the state of the insertion section 203. Where the number of detection points is four, as shown in FIG. 14, information on the insertion section 203 is acquired as below. That is, in this example, four detection points 605-1, 606-1, 607-1 and 608-1 are provided on the insertion section 203, as shown in FIG. 14. Where the insertion section 203 is inserted along the subject 910 from time t1 to time t2, the amount of movements $\Delta X51$, $\Delta X61$, $\Delta X71$ and $\Delta X81$ between the positions where the four detection points 605-1, 606-1, 607-1 and 608-1 are located at time t1 and the positions where the four positions 605-2, 606-2, 607-2 and 608-2 are located at time t2 are substantially equal to each other.

Where the insertion section 203 is inserted along the subject 910 from time t2 to time t3, as shown in FIG. 15, the amount of movements $\Delta X52$, $\Delta X62$, $\Delta X72$ and $\Delta X82$ between the positions where the four detection points 605-2, 606-2, 607-2 and 608-2 are located at time t2 and the positions where the four detection points 605-3, 606-3, 607-3 and 608-3 are located at time t3 are substantially equal to each other.

Figure 16:
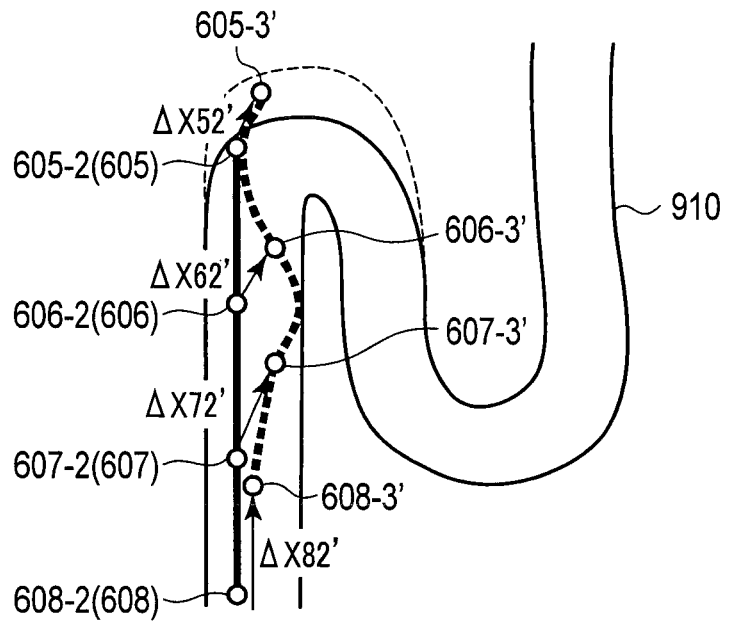
FIG. 16 illustrates the first variant of the first state determination method and schematically illustrates another example of how the insertion section is moved from time t2 to time t3.

On the other hands, where the insertion section 203 is not inserted along the subject 910 from time t2 to time t3, as shown in FIG. 16, the amount of movements $\Delta X52'$, $\Delta X62'$, $\Delta X72'$ and $\Delta X82'$ between the positions where the four detection points 605-2, 606-2, 607-2 and 608-2 are located at time t2 and the positions where the four detection points 605-3', 606-3', 607-3' and 608-3' are located at time t3 are not equal to each other. More specifically, the first amount of movement $\Delta 52'$ of the foremost detection point 605 of the detection points, the second amount of movement $\Delta 62'$ of the second detection point 606 which is in the second from the distal end, the third amount of movement $\Delta 72'$ of the third detection point 607 which is in the third from the distal end and the fourth amount of movement $\Delta 82'$ of the most rear-side detection point 608 of the detection points differ from each other. The first amount of movement $\Delta 52'$ and the second amount of movement $\Delta 62'$ are approximately equal to each other, the third amount of movement $\Delta 72'$ and the fourth amount of movement $\Delta 82'$ are approximately equal to each other, and the second amount of movement $\Delta 62'$ and the third amount of movement $\Delta 72'$ differ greatly from each other and satisfy $|\Delta 62'|<|\Delta 72'|$. From these results, it can be determined that a buckle occurs between the second detection point 606 and the third detection point 607. Where the number of detection points is large, the amount of information increases, accordingly. As a result, detailed information on the state of the insertion section 203 can be obtained. If the number of detection points is large, the portion of the insertion section 203 where abnormality (e.g., a buckle) occurs can be specified.

[Second Variant]

Figure 17:
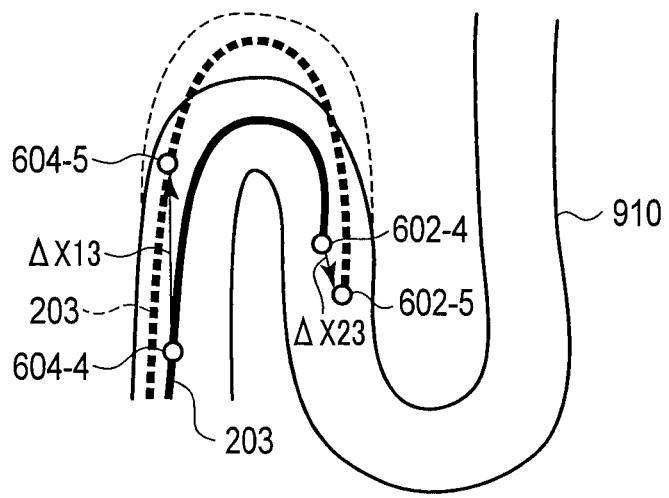
FIG. 17 illustrates a second variant of the first state determination method and schematically illustrates an example of how an insertion section is moved.

When the distal end of the insertion section 203 gets struck although the rear end portion of the insertion section 203 is inserted, the insertion section 203 may be buckled in the subject, but this is not the only phenomenon the state shows. That is, for example, a flexure of the subject may be deformed (extended) by the insertion section 203, as shown in FIG. 17. In FIG. 17, the shape which the insertion section 203 takes at time t4 and the shape which the insertion section 203 takes at time t5 which is after time t4 by $\Delta t$ are schematically illustrated. In this case as well, the second amount of movement $\Delta X23$, which is the difference between the position 602-4 where the foremost end is located at time t4 and the position 602-5 where the foremost end is located at time t5, is shorter than the first amount of movement $\Delta X13$, which is the difference between the position 604-4 where the rear end is located at time t4 and the position 604-5 where the rear end is located at time t5. That is, the degree of interrelation of the amounts of movement between the two detection points is low.

As described above, the first state determination method enables detection of not only a buckle but also a change in the insertion state that is not intended as a detection target, such as the deformation of the subject 910 caused by the insertion section 203.

[Second State Determination Method]

In the second state determination method, the state of the insertion section 203 is determined based on how the position of a characteristic attention point, specified by the shape, moves with time.

Figure 18:
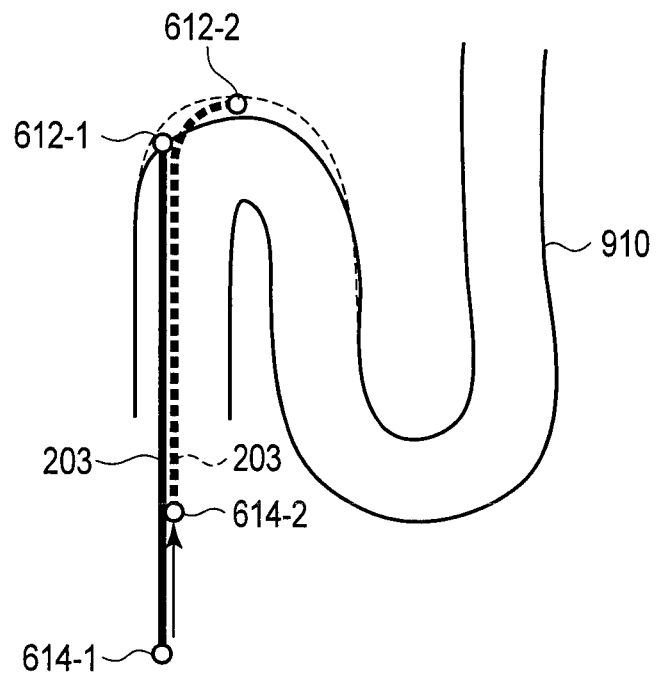
FIG. 18 illustrates a second state determination method and schematically illustrates how an insertion section is moved from time t1 to time t2.

In FIG. 18, the shape which the insertion section 203 takes at time t1 and the shape which the insertion section 203 takes at time t2 which is after time t1 by Δt are schematically illustrated. In this case, a discretionary point on the rear end portion of the insertion section 203 moves from first rear end position 614-1 to second rear end position 614-2. In the description below, it will be assumed that the discretionary point on the rear end portion is a position where a rear-side position sensor is located. The discretionary point will be referred to as a rear-side detection point. In the meantime, the distal end of the insertion section 203 moves from first distal end position 612-1 to second distal end position 612-2.

Figure 19:
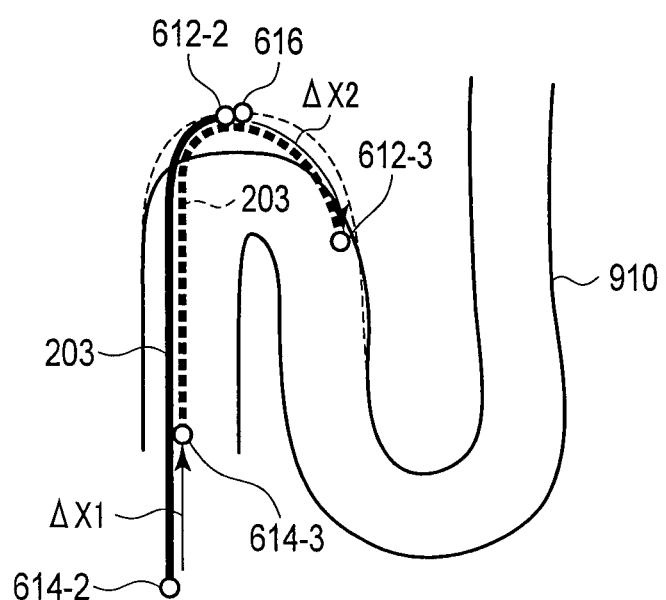
FIG. 19 illustrates the second state determination method and schematically illustrates an example of how the insertion section is moved from time t2 to time t3.

In FIG. 19, the shape which the insertion section 203 takes at time t2 and the shape which the insertion section 203 takes at time t3 (which is after time t2 by Δt) are schematically illustrated. In the case shown in FIG. 19, the insertion section 203 is inserted along the subject 910. That is, the rear-side detection point of the insertion section 203 moves for a distance of ΔX1 from second rear end position 614-2 to third rear end position 614-3. At the time, the distal end of the insertion section 203 moves along the insertion section 203 for a distance of ΔX2 from second distal end position 612-2 to third distal end position 612-3.

The turn-around point of the bending portion of the insertion section 203 (the point depicted as being located uppermost of the bend in FIG. 19) is determined as an attention point 616. In this case, the shape of the insertion section 203 is first specified, and then the position of the attention point 616 is specified.

In the case shown in FIG. 19, the position of the attention point 616 remains at the same position even if the position of the rear-side detection point of the insertion section 203 changes. That is, in the period from time t2 to time t3, the insertion section 203 is inserted along the subject 910; in other words, the insertion section 203 slides in the longitudinal direction thereof. Therefore, the attention point 616 remains at the same position from time t2 to time t3.

Figure 20:
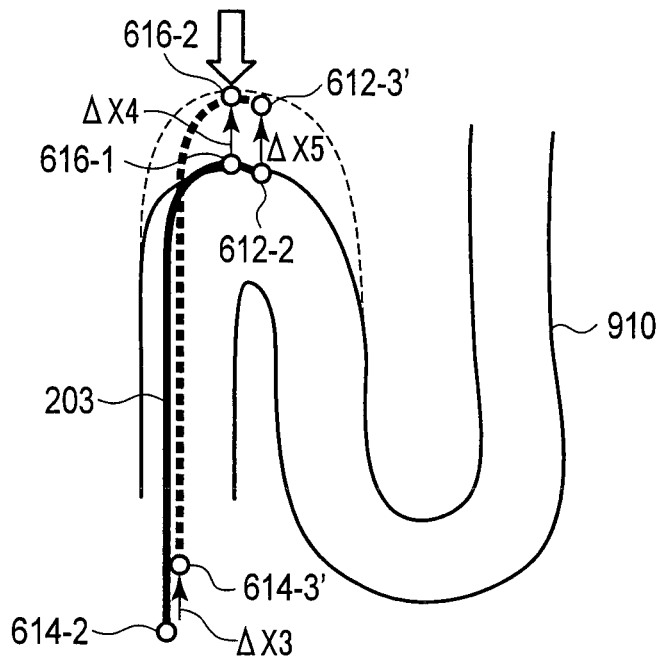
FIG. 20 illustrates the second state determination method and schematically illustrates another example of how the insertion section is moved from time t2 to time t3.

In FIG. 20, the shape which the insertion section 203 takes at time t2 and the shape which the insertion section 203 takes at time t3 which is after time t2 by Δt are schematically illustrated as another possible state. In the case shown in FIG. 20, the insertion section 203 is not inserted along the subject 910. In this case, the rear-side detection point of the insertion section 203 moves for a distance of ΔX3 from second rear end position 614-2 to third rear end position 614-3'. At the time, the distal end of the insertion section 203 moves upward in FIG. 20 for a distance of ΔX5 from second distal end position 612-2 to third distal end position 612-3'.

The state shown in FIG. 20 takes place, for example, if the distal end of the insertion section 203 is caught by the subject 910 and the insertion section 203 cannot move in the longitudinal direction thereof. In this case, the subject 910 is pushed in accordance with the insertion of the insertion section 203. As a result, the position of the attention point 616 changes for a distance of ΔX4 from first position 616-1 to second position 616-2 in the direction toward the turn-around point of the insertion section 203, in accordance with the movement of the rear-side detection point of the insertion section 203. That is, the subject 910 is extended.

In the state shown in FIG. 20, a shape of the insertion section 203 maintains a "stick shape", and the subject 910 is pushed up by the "handle" of the "stick". This state will be referred to as a stick state.

As should be apparent from the comparison between the case shown in FIG. 19 and the case shown in FIG. 20, a determination can be made as to whether or not the insertion section 203 is inserted along the subject, based on the variation in the position of the attention point. In the example described above, it is shown that the insertion section 203 move in parallel in the stick state. However, if the insertion section 203 is deformed, the amount of movement of the rear-side detection point and the amount of movement of the attention point differ from each other. In addition, how the subject 910 is extended can be determined based on how the position of the attention point changes. Where the subject is extended, the insertion section 203 pushes or presses the subject 910. That is, as indicated by the outlined arrow in FIG. 20, the subject 910 presses the insertion section 203. Conversely, the insertion section 203 pushes back the subject 910. Accordingly, the level of pressing applied to the subject can be determined based on the variation in how the position of the attention point.

Figure 21:
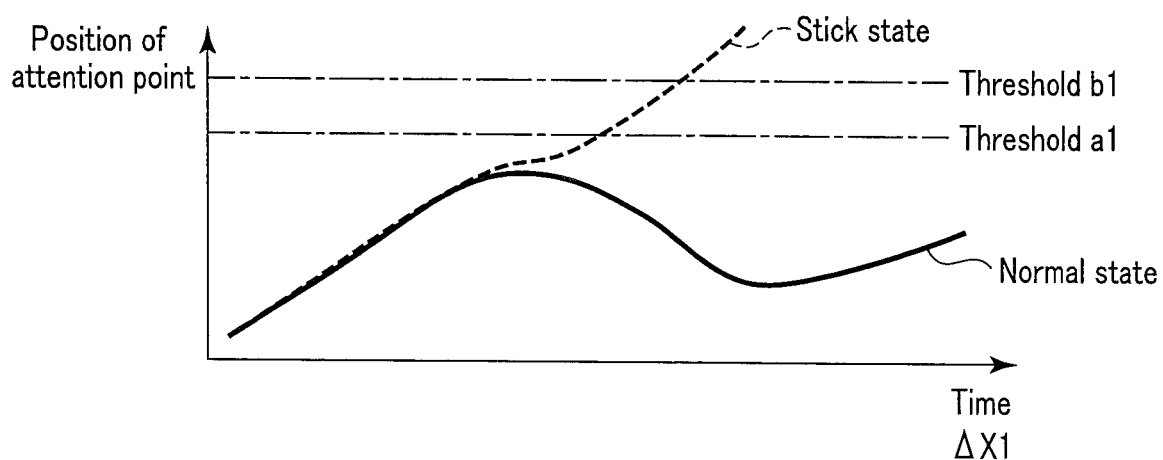
FIG. 21 illustrates how an attention point changes its position with time.

FIG. 21 shows how the position of an attention point changes with time or in relation to the amount of movement ΔX1 of a detection point. In FIG. 21, the position of the attention point is indicated, with the direction toward the turn-around point being shown as the plus direction. When the insertion section 203 is inserted normally, as indicated by the solid line, the position of the attention point fluctuates in such a manner that the value of the position of the attention point is smaller than threshold a1 at all times. When the insertion section 203 is in the stick state, as indicated by the broken line, the position of the attention point changes in such a manner that the value of the position exceeds threshold a1.

With respect to the value of the position of the attention point, thresholds a1 and b1 can be properly determined. For example, threshold a1 may be a value in response to which a warning indicating that the subject 910 begins to extend is issued, and threshold b1 may be a value in response to which a warning indicating that further extension of the subject 910 is dangerous is issued. With the thresholds being determined properly, information on the position of the attention point can be used as information for supporting the operation of the endoscope 200, including a warning to the user and a warning signal output to the controller 310.

Let us assume that second operation support information α2 is introduced as a value representing the state of the insertion section 203 described above. The second operation support information α2 is defined as follows:

$$\alpha 2 \equiv |\Delta Xc|/|\Delta Xd|$$

where ΔXc is a displacement of the attention point and ΔXd is a displacement of the rear-side detection point. The second operation support information α2 indicates that the closer to 0 the value of the second operation support information α2 is, the more properly the insertion section 203 is inserted along the subject 910, and the closer to 1 the value of the second operation support information α2 is, the more strongly the insertion section 203 pushes the subject 910.

The second operation support information α2 may be defined as follows:

$$\alpha 2 \equiv (\Delta Xc + C2)^L / (|\Delta Xd| + C1)^M$$

where C1, C2, L and M are any real numbers.

By way of example, let us consider the case where Nd<k1·P (1≥k2>>k1≥0) is satisfied, where Nd and Nc (Nd, Nc≥0) denote detection noise component levels of ΔXd and ΔXc, P denotes how the insertion section pushes the subject when it comes into contact with the subject and without application of a load, and k1 and k2 denote parameters (1≥k2>>k1≥0).

When |ΔXd|<k2·P at a given time, ΔXd and ΔXc are calculated, with the time periods or the moving amounts corresponding to a predetermined number of times until the given time being accumulated, in such a manner as to attain the state where |ΔXd|≥k2·P. In the state where |ΔXd|≥k2·P, parameters C1, C2, L and M are determined as follows:

$$C1 = -Nd$$

$$C2 = Nc$$

$$L = M = 2$$

As N1 and N2, values which are approximately three times as large as the standard deviations (σ) of noise levels may be used.

By determining the settings as above, the second operation support information α2 is obtained which takes into account the effects of noise for a certain movement and reduces the adverse effects of detection failure. In addition, by performing measurement in such a manner as to satisfy k2·P<<|ΔXd|<P, the second operation support information α2 ensures no load or light load on the subject. The way for reducing the adverse effects of noise can be applied to the calculation of other support information.

FIG. 22 schematically illustrates a configuration example of the operation supporting apparatus which can be employed for implementing the second state determination method.

The insertion/removal supporting apparatus 100 comprises a position acquisition unit 110, a shape acquisition unit 120, a state determination unit 130 and a support information generation unit 180. The detection point acquisition unit 111 of the position acquisition unit 110 acquires the position of a detection point where the position sensor on the rear end side of the insertion section 203 is arranged, based on information output from the sensor 201. The shape acquisition unit 120 acquires the shape of the insertion section 203, based on information output from the sensor 201. The attention point acquisition unit 121 of the shape acquisition unit 120 acquires the position of an attention point, which is the turn-around point of a bending portion of the insertion section 203, based on the shape of the insertion section 203.

The state determination unit 130 includes a displacement acquisition unit 151, a displacement information calculation unit 152 and an attention-point state determination unit 153. The displacement acquisition unit 151 calculates a displacement of an attention point, based on how the position of the attention point changes with time and displacement analysis information 192-3 stored in the program memory 192. The displacement acquisition unit 151 calculates a displacement of a detection point, based on how the position of the detection point changes with time and displacement analysis information 192-3 stored in the program memory 192. As described above, the displacement acquisition unit 151 functions as a first displacement acquisition unit for acquiring the first displacement of the attention point and also functions as a second displacement acquisition unit for acquiring the second displacement of the detection point.

The displacement information calculation unit 152 calculates displacement information based on both the calculated displacement of the attention point and the calculated displacement of the detection point. The attention-point state determination unit 153 calculates a state of the attention point, based on the calculated displacement information and support-information determination reference information 192-4 stored in the program memory 192.

The support information generation unit 180 generates operation support information, based on the determined state of the attention point. The operation support information is fed back to the control of the controller 310, is displayed on the display 320, or is stored in the recording device 196.

Figure 23:
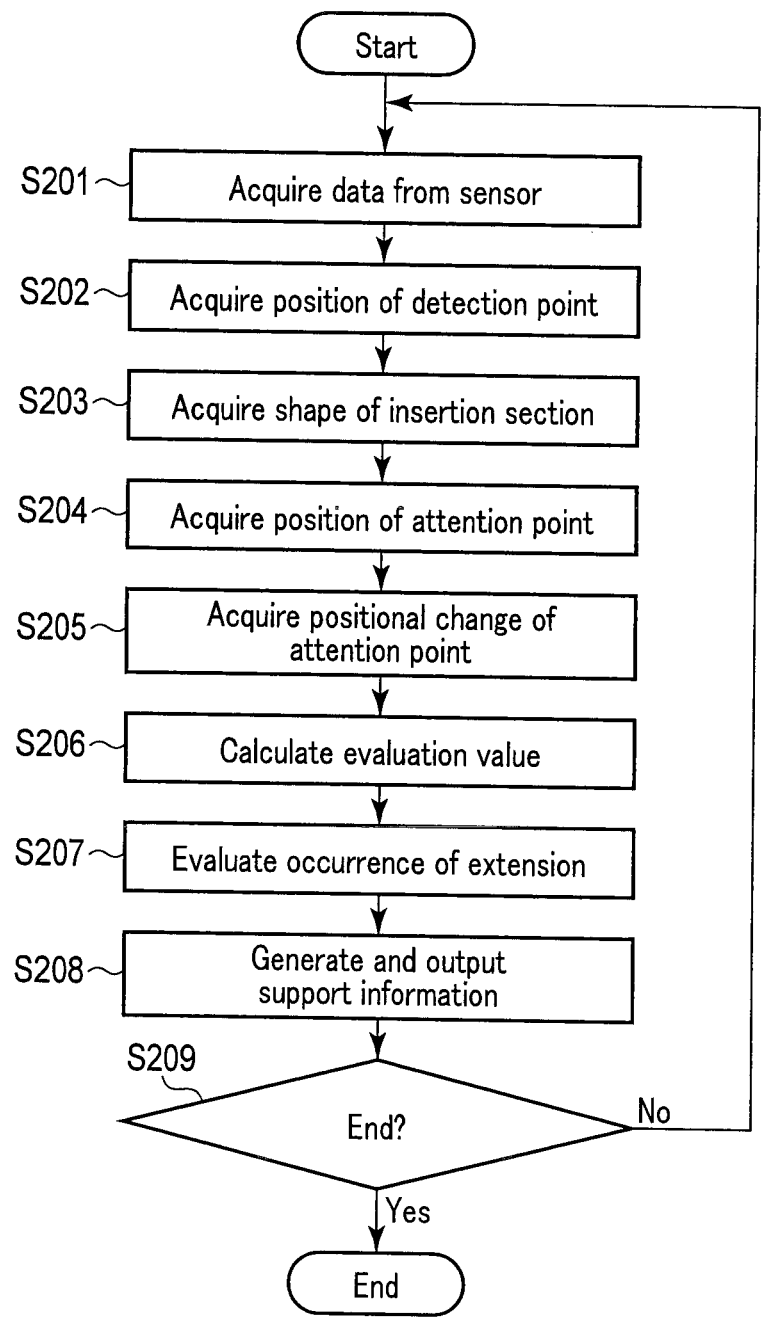
FIG. 23 is a flowchart illustrating an example of processing performed in the second state determination method.

How the insertion/removal supporting apparatus 100 operates in the second state determination method will be described with reference to the flowchart shown in FIG. 23.

In step S201, the insertion/removal supporting apparatus 100 acquires output data from the sensor 201. In step S202, the insertion/removal supporting apparatus 100 acquires the position of a rear-side detection point, based on the data acquired in step S201.

In step S203, the insertion/removal supporting apparatus 100 acquires the shape of the insertion section 203, based on the data acquired in step S201. In step S204, the insertion/removal supporting apparatus 100 acquires the position of an attention point, based on the shape of the insertion section 203 acquired in step S203.

In step S205, the insertion/removal supporting apparatus 100 acquires how the position of the attention point moves with time. In step S206, the insertion/removal supporting apparatus 100 calculates an evaluation value of the positional change of the attention point, such as the second operation support information α2, based on the positional change the detection point and the positional change of the attention point. In step S207, the insertion/removal supporting apparatus 100 perform evaluation of extension such as whether an extension occurs in the vicinity of the attention point, and if the extension occurs, evaluates the degree of extension, based on the evaluation value calculated in step S206.

In step S208, the insertion/removal supporting apparatus 100 generates proper support information to be used in later processing, based on the determination result representing whether the extension of the subject occurs and on the second operation support information α2 etc., and outputs the support information, for example, to the controller 310 and the display 320.

In step S209, the insertion/removal supporting apparatus 100 determines whether a termination signal for terminating the processing is entered. Unless the termination signal is entered, the processing returns to step S201. That is, the processing mentioned above is repeated until the termination signal is entered, and operation support information is output. If the termination signal is entered, the processing is brought to an end.

The use of the second state determination method enables the displacement of an attention point to be specified, and operation support information representing whether the extension of the subject is occurred or not is generated based on the displacement of the attention point. In the above example, it is shown that the operation support information is generated by directly sensing the position of the rear-side detection point. However, the present invention is not limited to this. The operation support information may be generated using information on attention points, namely any points of the insertion section 203. Where the positions of attention points are used, the positions of the attention points are acquired not by the detection point acquisition unit 111 but by the position acquisition unit 110, and the positions of the acquired attention points are used. In the other respects, the processing is similar to that described above.

[Variant]

An attention point may be any point of the insertion section 203. If the shape of the insertion section 203 has a specific feature, and an attention point can be specified based on the shape, the attention point may be any point of the insertion section 203. For example, as shown in FIG. 24, not only a first attention point 617 specified by a bend initially generated when the insertion section 203 is inserted into the subject 910 but also a second attention point 618 specified by a bend subsequently generated when the insertion section 203 is inserted further, may be analyzed. When the insertion section 203 is inserted, there may be a case where the first attention point 617 remains at the same position whereas the second attention point 618 changes in position, as shown in FIG. 25, for example. In this case, the second state determination method generates a determination result indicating that no extension is generated at the first attention point 617 and an extension is generated at the second attention point 618, based on the amount of movement $\Delta X1$ of the rear-side detection point and the amount of movement $\Delta X2$ of the second attention point 618, and outputs the determination result as operation support information.

The attention point may be any point as long as it is a characteristic point determined based on the shape of the insertion section 203. For example, the attention point may be the turn-around point of a bend, as in the above example. Alternatively, it may be the start position of the bend, or any point (e.g., a middle point) of the straight portion between the bend and the distal end of the insertion section 203. Where the insertion section 203 has two bends, the attention point may be an intermediate point between the two bends. In any case, operation support information is output, in a similar manner to that of the examples described above. Although the detection point is described as any point on the rear end portion of the insertion section 203, this is not restrictive. The position of the detection point may be any point of the insertion section 203.

[Third State Determination Method]

In the third state determination method, the state of the insertion section 203 is determined based on how the position of an attention point changes in the insertion section 203.

Figure 26:
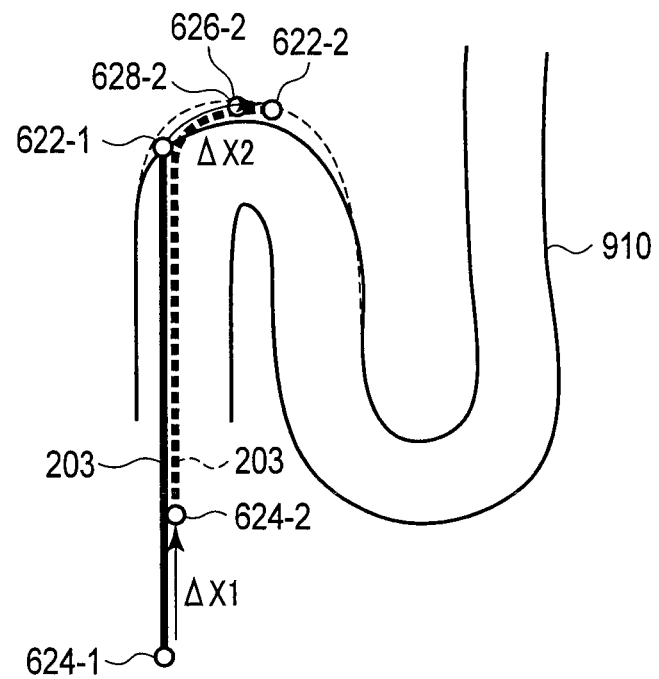
FIG. 26 illustrates a third state determination method and schematically illustrates how an insertion section is moved from time t1 to time t2.

In FIG. 26, the shape which the insertion section 203 takes at time t1 and the shape which the insertion section 203 takes at time t2 which is after time t1 by $\Delta t$ are schematically illustrated. In this case, a discretionary point on the rear end portion of the insertion section 203 moves by distance $\Delta X1$ from first rear end position 624-1 to second rear end position 624-2. In the description below, it is assumed that the discretionary point on the rear end portion is a position where a position sensor is arranged. This point will be referred to as a rear-side detection point. In the meantime, the distal end of the insertion section 203 moves by distance $\Delta X2$ from first distal end position 622-1 to second distal end position 622-2. Ideally, distance $\Delta X1$ and distance $\Delta X2$ are equal to each other. The turn-around point of the bending portion which the insertion section 203 takes at time t2 is determined as an attention point 626-2. The point of the insertion section 203 located at the same position as the attention point 626-2 will be referred to as a second point 628-2. The second point 628-2 can be represented by the distance by which it is away from the distal end of the insertion section 203, as viewed in the longitudinal axis of the insertion section 203.

Figure 27:
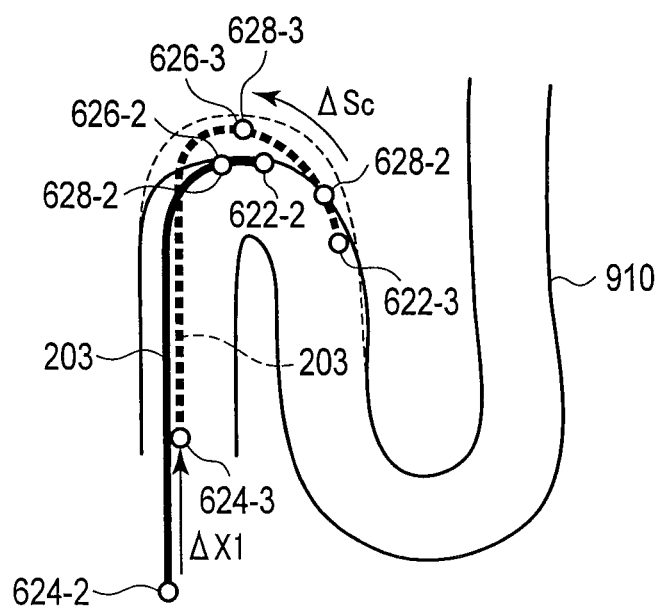
FIG. 27 illustrates the third state determination method and schematically illustrates an example of how the insertion section is moved from time t2 to time t3.

In FIG. 27, the shape which the insertion section 203 takes at time t2 and the shape which the insertion section 203 takes at time t3 which is after time t2 by $\Delta t$ are schematically illustrated. In the case shown in FIG. 27, the insertion section 203 is inserted substantially along the subject 910. In this case, the rear-side detection point of the insertion section 203 is inserted by distance $\Delta X1$.

The turn-around point of the bending portion which the insertion section 203 takes at time t3 is determined as an attention point 626-3. The point on the insertion section 203 which is moved together in accordance with the insertion or removal of the insertion section 203, which is away from the distal end constantly by the same distance, and which is located at the same position as the attention point 626-3 will be referred to as a third point 628-3. Like the second point 628-2, the third point 628-3 can be represented by the distance by which it is away from the distal end of the insertion section 203.

In the example shown in FIG. 27, the point indicating the position of the attention point 626 of the insertion section 203 moves from the second point 628-2 to the third point 628-3 from time t2 to time t3. In terms of the relative position as expressed from the distal end of the insertion section 203, the point indicating the attention point 626 moves rearward along the insertion section 203 by $\Delta Sc$. When the insertion section 203 is inserted along the subject completely, the displacement $\Delta Sc$ of the attention point 626 of the insertion section 203 from the second point 628-2 to the third point 628-3 is equal to the displacement $\Delta X1$ of the rear-side detection point of the insertion section 203. The state where the insertion section 203 is inserted along the subject will be referred to as a state where the insertion section 203 has self-following property.

Even when the insertion section 203 is not inserted completely along the subject, there may be a case where the insertion section 203 can be regarded as being substantially along the subject. In such a case, the displacement $\Delta Sc$ from the second point 628-2 to the third point 628-3 is substantially equal to the displacement $\Delta X1$ of the rear-side detection point of the insertion section 203. In such a case, the self-following property can be regarded as high.

FIG. 28 schematically illustrates the shapes the insertion section 203 takes at times t2 and t3 where the insertion section 203 is not inserted along the subject 910. In this case as well, the rear-side detection point of the insertion section 203 is inserted by distance $\Delta X1$. In the case shown in FIG. 28, the insertion section 203 is in the stick state, and the subject 910 is extended.

Where the turn-around point of the bend which the insertion section 203 has at time t3 is determined as an attention point 626-3', the point of the insertion section 203 located at the same position as the attention point 626-3' will be referred to as a third point 628-3'. The point indicating the position of the attention point 626 of the insertion section 203 moves rearward by $\Delta Sc'$ along the insertion section 203 from the second point 628-2 to the third point 628-3'.

When the insertion section 203 is not completely along the subject, the point indicating the position of the attention point 626 of the insertion section 203 moves from the second point 628-2 to the third point 628-3', and its displacement $\Delta Sc'$ is far shorter than the displacement $\Delta X1$ of the rear-side detection point of the insertion section 203.

As described above, a determination is made as to whether or not the insertion section 203 is inserted along the subject, based on the insertion amount of the insertion section 203 and the positional change of the attention point of the insertion section 203. When the insertion amount of the insertion section 203 and the positional change of the attention point of the insertion section 203 are related, it is made clear that the insertion section 203 is inserted along the subject 910. When the insertion amount of the insertion section 203 and the positional change of the attention point of the insertion section 203 are not related, it is made clear that the insertion section 203 is not inserted along the subject 910.

Figure 30:
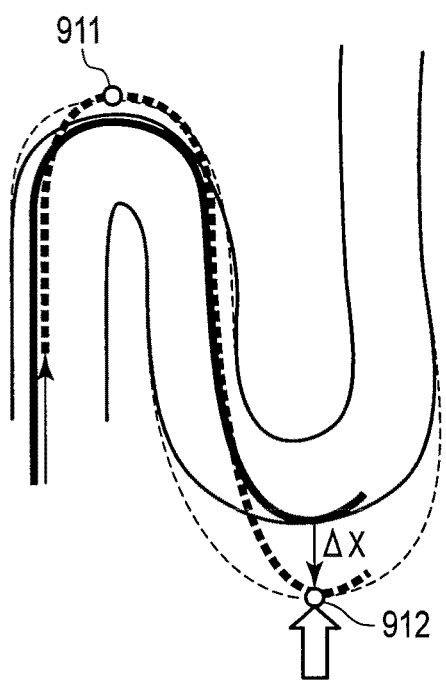
FIG. 30 illustrates the third state determination method and schematically illustrates an example of how an insertion section is moved.

FIGS. 29 and 30 illustrate examples of how the insertion section 203 is after it is inserted along the subject 910 as shown in FIG. 27. In FIG. 29, the insertion section 203 is inserted along the subject 910 at the first flexure 911 shown in the upper portion, and the distal end of the insertion section 203 reaches the second flexure 912 shown in the lower portion. In FIG. 30, the insertion section 203 is inserted along the subject 910 at the first flexure 911, and the insertion section 203 is not inserted along the subject 910 but is in the stick state at the second flexure 912.

Figure 31:
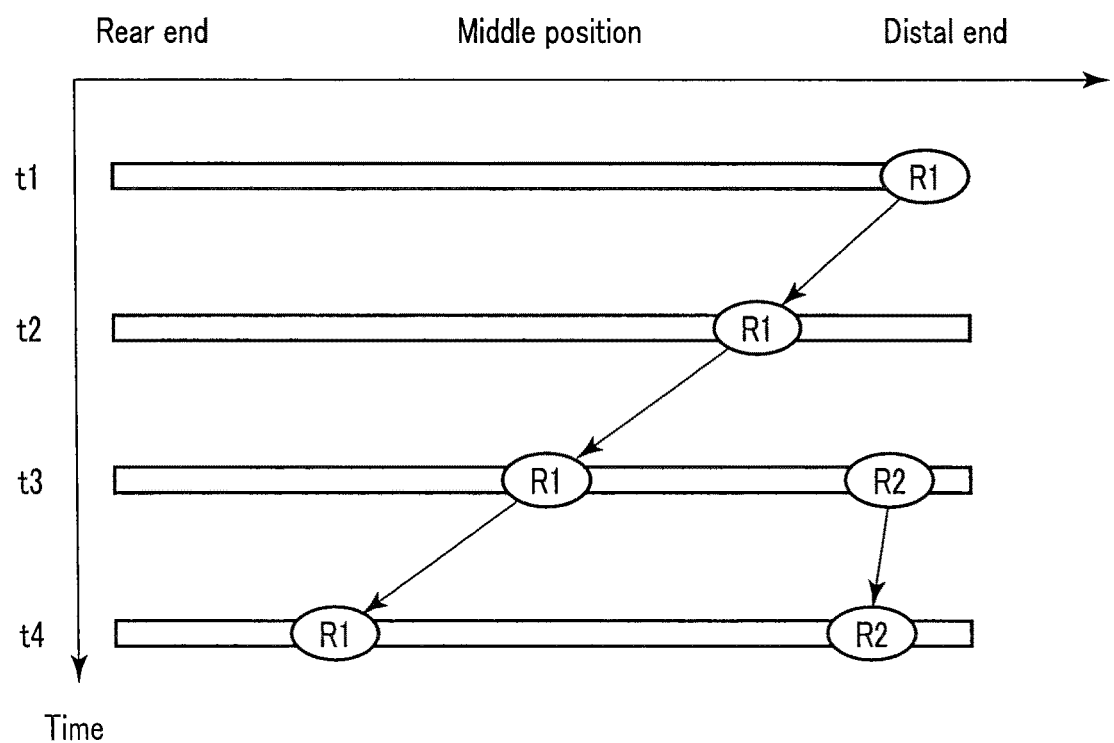
FIG. 31 schematically illustrates how an attention point of an insertion section changes its position.

FIG. 31 schematically illustrates how positions of attention points of the insertion section 203 change their positions in the case shown in FIGS. 29 and 30. When the insertion section 203 is gradually inserted from the insertion port of the subject 910 with time t1, t2, t3 and t4 in sequence, the first attention point R1 corresponding to the first flexure 911 initially detected moves rearward in accordance with an increase in the insertion amount.

The second attention point R2 corresponding to the second flexure 912 is detected at time t3, as shown in FIG. 31. The second attention point R2 does not move rearward even when the insertion amount is increasing. The shape which the insertion section 203 has at the second attention point R2 can be changed back to the original shape. As described above, the points determined based on the attention points change in position differently between portions having high self-following property and portions having low self-following property.

Figure 32:
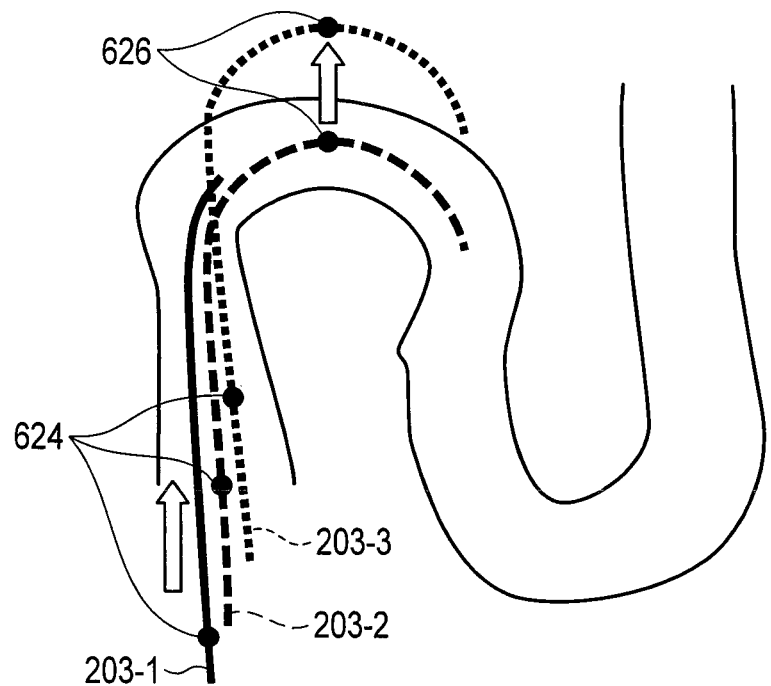
FIG. 32 schematically illustrates an example of how an insertion section is moved.

The third state determination method will be described in more detail with reference to FIGS. 32 to 35. Let us assume that the insertion section 203 changes its state with time in the order of the first state 203-1, the second state 203-2 and the third state 203-3, as shown in FIG. 32. Consideration will be given of the case where the insertion section 203 is inserted along the subject 910 from the first state 203-1 to the second state 203-2 and pushes upward and extends the subject 910 from the second state 203-2 to the third state 203-3.

Figure 33:
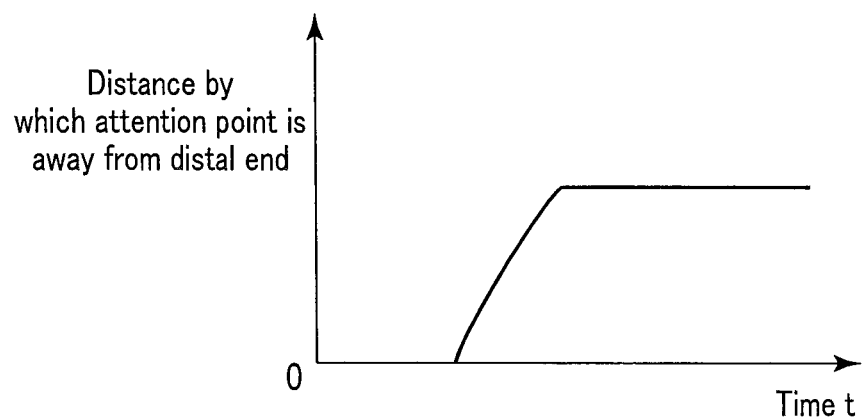
FIG. 33 illustrates an example of how the distance between an attention point and the distal end of an insertion section changes with time.

This case is illustrated in FIG. 33, in which the abscissa axis represents the passage of time, namely the positional change of the rear-side detection point 724, and the ordinate axis represents the attention point 626 of the insertion section 203, namely, the distance by which the attention point 626 is away from the distal end. As shown in FIG. 33, the detection point is not detected for a certain time from the start of insertion, as in the first state 203-1. When the insertion section 203 is inserted along the subject 910, as in the period of time from the first state 203-1 to the second state 203-2, the distance of the attention point from the distal end gradually increases, as indicated in FIG. 33. When the insertion section 203 is in the stick state, as in the period of time from the second state 203-2 to the third state 203-3, the distance of the attention point from the distal end is constant, as indicated in FIG. 33.

Figure 35:
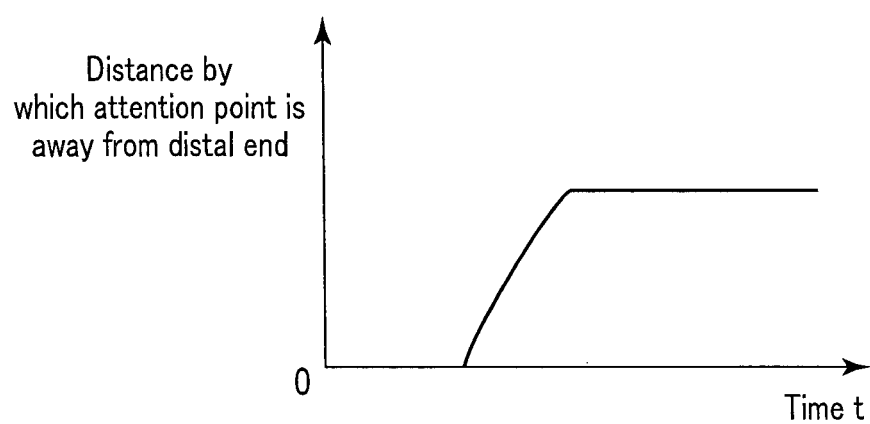
FIG. 35 illustrates another example of how the distance between the attention point and the distal end of the insertion section changes with time.

Consideration will be given of the case where the insertion section 203 is inserted along the subject 910 from the first state 203-1 to the second state 203-2 and obliquely pushes the subject 910 from the second state 203-2 to the third state 203-3. This case is illustrated in FIG. 35, in which the abscissa axis represents the passage of time, namely the positional change of the rear-side detection point 624, and the ordinate axis represents the attention point 626 of the insertion section 203, namely, the distance by which the attention point 626 is away from the distal end. The data shown in FIG. 35 is similar to that shown in FIG. 33.

The criterion formula representing the self-following property R is defined as follows:

$$R = |\Delta Sc|/|\Delta X1|$$

where $\Delta Sc$ is a moving amount for which an attention point moves along the shape of the insertion section 203, and $\Delta X1$ is an amount of movement for which a detection point, any point on the rear end portion of the insertion section 203, moves. This case is expressed in FIG. 36, in which the abscissa axis represents the passage of time or the amount of movement $\Delta X1$ by which any point moves (namely the insertion amount), and the ordinate axis represents the self-following property R. When the insertion section 203 is inserted normally along the subject, the self-following property R takes values which are close to 1, as indicated by the solid line. On the other hand, when the insertion section 203 is in the stick state, the self-following property R takes values far smaller than 1.

The self-following property R may be defined as follows:

$$R = (\Delta Sc + C2)^L / (|\Delta X1| + C1)^M$$

where C1, C2, L and M are any real numbers.

Assuming that the detection noise component levels of $\Delta X1$ and $\Delta Sc$ are N1 and Nc (N1, Nc≥0), parameters C1, C2, L and M are defined as follows:

$$C1 = N1 \quad |\Delta X1| \geq N1$$
$$C2 = -Nc \quad |\Delta X2| \geq Nc$$
$$\quad = -|\Delta X2| \quad |\Delta X2| < Nc$$
$$L = M = 4$$

As N1 and Nc, values which are approximately three times as large as the standard deviations (σ) of noise levels may be set.

In the measure against noise, C1 is positive and C2 is negative, as above, and by taking such a measure, the self-following property R can be operation support information is obtained which reduces the adverse effects caused by the detection noise and lessens the detection errors caused by the detection noise. Where the orders of L and M are 2 or more, a decrease in the ratio of $\Delta Sc$ to $\Delta X1$ can be sensitively detected, and a determination can be easily made as to whether or not the self-supporting property is degraded. The way for reducing the adverse effects of noise can be applied to the calculation of other support information.

Figure 36:
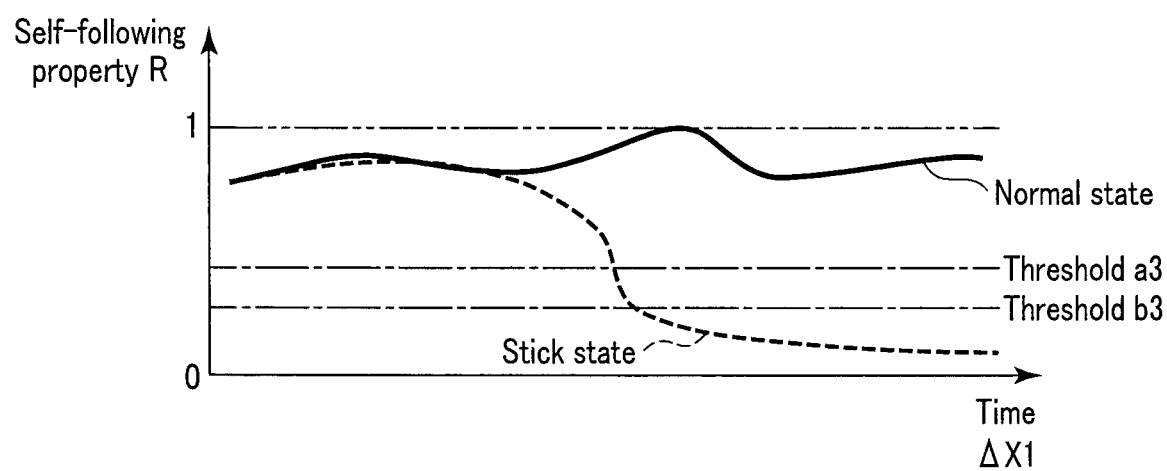
FIG. 36 illustrates an example of how self-following property changes with time.

As shown in FIG. 36, with respect to the self-supporting property R, thresholds a3 and b3 can be properly determined. For example, threshold a3 may be a value in response to which a warning indicating that the subject 910 begins to extend is issued, and threshold b3 may be a value in response to which a warning indicating that further extension of the subject 910 is dangerous is issued. With the thresholds being determined properly, the value of the self-supporting property R can be used as information for supporting the operation of the endoscope 200, including a warning to the user and a warning signal supplied to the controller 310.

FIG. 37 schematically illustrates a configuration example of the operation supporting apparatus which can be employed for implementing the third state determination method.

The insertion/removal supporting apparatus 100 comprises a position acquisition unit 110, a shape acquisition unit 120, a state determination unit 130 and a support information generation unit 180. The detection point acquisition unit 111 of the position acquisition unit 110 acquires the position of a detection point where the position sensor on the rear end side of the insertion section 203 is arranged, based on information output from the sensor 201.

The shape acquisition unit 120 acquires the shape of the insertion section 203, based on information output from the sensor 201. The attention point acquisition unit 121 of the shape acquisition unit 120 acquires the position of an attention point, based on the shape of the insertion section 203.

The state determination unit 130 includes a displacement acquisition unit 161, a displacement information calculation unit 162 and an attention-point state determination unit 163. The displacement acquisition unit 161 calculates how the position of an attention point changes in the insertion section 203, based on the shape of the insertion section 203, the position of the attention point and displacement analysis information 192-5 stored in the program memory 192. The displacement acquisition unit 161 calculates how the position of a detection point changes, based on the position of the rear-side detection point of the insertion section 203 and the displacement analysis information 192-5 stored in the program memory 192. As described above, the displacement acquisition unit 161 functions as a first displacement acquisition unit for acquiring the first displacement of the attention point and also functions as a second displacement acquisition unit for acquiring the second displacement of the detection point.

The displacement information calculation unit 162 compares the displacement of the attention point in the insertion section 203 with the displacement of the rear-side detection point in the insertion section 203, and calculates displacement information, using the displacement analysis information 192-5 stored in the program memory 192. The attention-point state determination unit 163 calculates a state of the attention point, based on the displacement information and determination reference information 192-6 stored in the program memory 192.

The support information generation unit 180 generates operation support information, based on the determined state of the attention point. The operation support information is fed back to the control of the controller 310, is displayed on the display 320, or is stored in the recording device 196.

Figure 38:
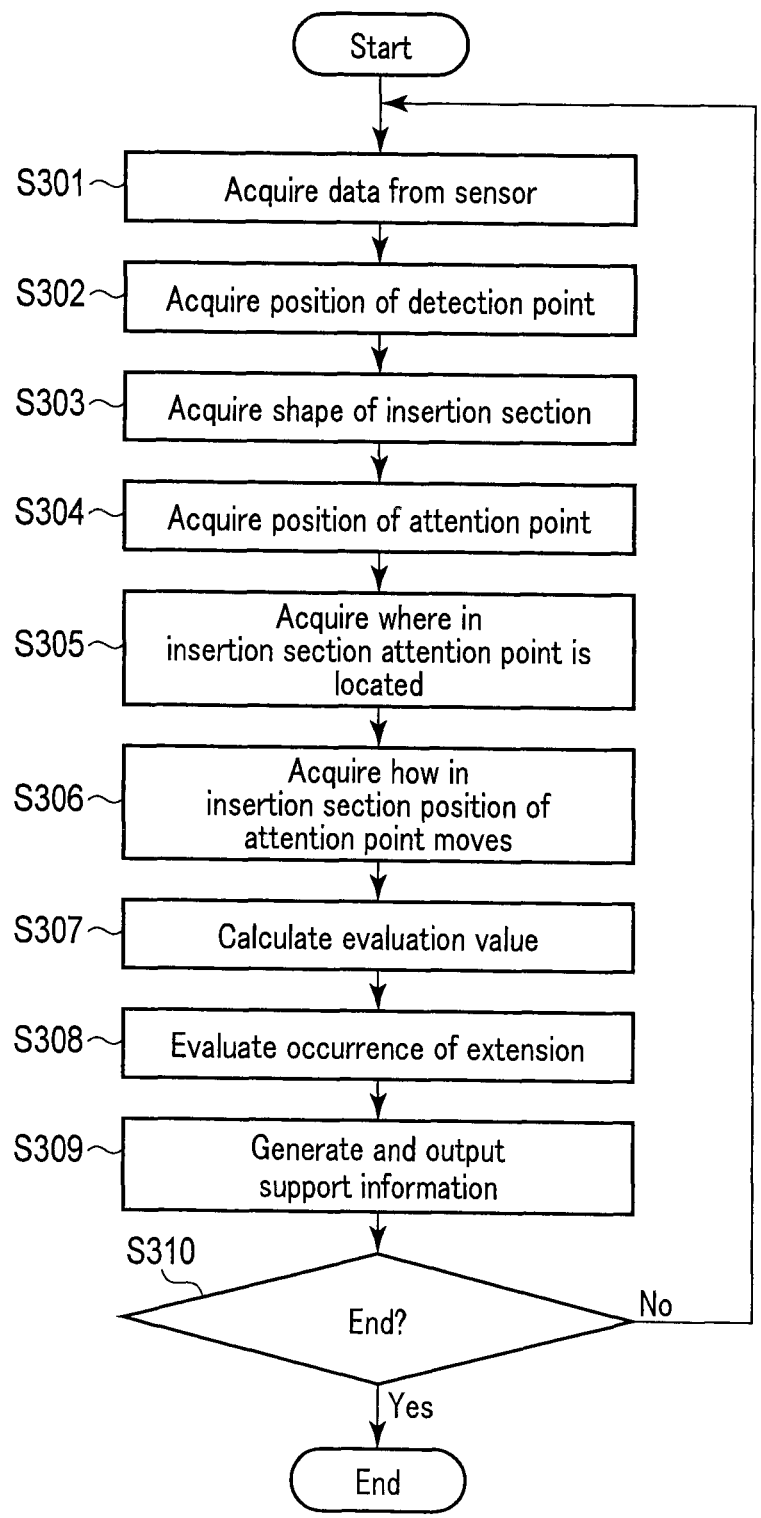
FIG. 38 is a flowchart illustrating an example of processing performed in the third state determination method.

How the insertion/removal supporting apparatus 100 operates in the third state determination method will be described with reference to the flowchart shown in FIG. 38.

In step S301, the insertion/removal supporting apparatus 100 acquires output data from the sensor 201. In step S302, the insertion/removal supporting apparatus 100 acquires the position of a rear-side detection point, based on the data acquired in step S301.

In step S303, the insertion/removal supporting apparatus 100 acquires the shape of the insertion section 203, based on the data acquired in step S301. In step S304, the insertion/removal supporting apparatus 100 acquires the position of an attention point, based on the shape of the insertion section 203 acquired in step S303.

In step S305, the insertion/removal supporting apparatus 100 calculates where in the insertion section 203 the attention point is located. In step S306, the insertion/removal supporting apparatus 100 acquires how the position of the attention point in the insertion section 203 moves with time. In step S307, the insertion/removal supporting apparatus 100 calculates an evaluation value representing how the position of the attention point changes in the insertion section 203 having self-following property R, based on the positional change of the detection point and the positional change of the attention point in the insertion section 203. In step S308, the insertion/removal supporting apparatus 100 perform evaluation of extension such as whether an extension occurs in the vicinity of the attention point and if the extension occurs, evaluates the degree of extension, based on the evaluation value calculated in step S307.

In step S309, the insertion/removal supporting apparatus 100 generates proper support information to be used in later processing, based on the determination result representing whether the extension of the subject occurs and on the self-supporting property R etc., and outputs the support information, for example, to the controller 310 and the display 320.

In step S310, the insertion/removal supporting apparatus 100 determines whether a termination signal for terminating the processing is entered. Unless the termination signal is entered, the processing returns to step S301. That is, the processing mentioned above is repeated until the termination signal is entered, and operation support information is output. If the termination signal is entered, the processing is brought to an end.

The use of the third state determination method enables the displacement of the attention point in the insertion section 203 to be specified, and operation support information representing whether the extension of the subject is occurred or not is generated based on the relations between the displacement and the insertion amount of the rear end portion of the insertion section 203, namely the displacement of the detection point, etc. The operation support information includes, for example, information representing the states of the insertion section 203 and subject 910, information representing whether the insertion section 203 pushes or presses the subject 910, information representing a level of pushing or pressing applied to the subject 910, etc. The operation support information also includes information representing whether the insertion section 203 or the subject 910 is in an abnormal state.

Like the attention points used in the second state determination method, the attention points used in the third state determination method may be any points as long as they are characteristic points determined based on the shape of the insertion section 203. For example, an attention point may be the turn-around point of a bending portion, as in the above example. Alternatively, it may be the start position of the bending portion, or any point (e.g., a middle point) of the straight portion between the bending portion and the distal end. Where the insertion section 203 has two bending portions, the attention point may be an intermediate point between the two bending portions. A detection point is not limited to a point on the rear end portion but may be any point. Instead of the detection point, an attention point (i.e., any point) may be used. Where attention points are used, the positions of the attention points are acquired not by the detection point acquisition unit 111 but by the position acquisition unit 110, and the positions of the acquired attention points are used.

[Variant]

In a variant of the third state determination method, the state of the insertion section 203 is determined based on the amount of movement for which the insertion section 203 moves in a tangential direction of the shape of the insertion section 203. In particular, the state of the insertion section 203 is determined based on the amount of movement for which an attention point moves in the tangential direction.

As schematically illustrated in FIG. 39, an attention point 631 is acquired based on the shape of the insertion section 203. Subsequently, a tangential direction 632 of the insertion section 203 is specified at the attention point 631, based on the shape of the insertion section 203. In the variant of the third state determination method, self-following property is evaluated based on the relations between the moving direction of the point on the insertion section 203 corresponding to the attention point 631 and the tangential direction 632. That is, the higher the degree of coincidence between the moving direction of the point of the insertion section 203 corresponding to the attention point 631 and the tangential direction 632 of the insertion section 203 is, the higher will be the self-following property.

As shown in FIG. 40, the state of the insertion section 203 and the state of the subject 910 are evaluated, for example, based on the ratio of $\Delta Sr/\Delta X$, where $\Delta X$ is a displacement of a point corresponding to the attention point, and $\Delta Sr$ is a displacement of that displacement in the tangential direction. That is, the state of the insertion section 203 and the state of the subject 910 are evaluated based on the angle $\theta$ which is formed between the tangential direction and the moving direction at the attention point.

Let us assume that the insertion section 203 changes its state with time in the order of the first state 203-1, the second state 203-2 and the third state 203-3, as shown in FIG. 32. FIG. 41 shows $|\Delta Sr|/|\Delta X|$ in this case, which represents how the ratio of the displacement in the tangential direction to the displacement of the insertion section 203 changes with time. In the period of time from the first state 203-1 to the second state 203-2, the self-following property is high, so that the ratio of the displacement of a given point in the tangential direction to the displacement of the given point in the moving direction is approximately equal to 1 when the insertion section 203 changes its position. On the other hands, in the period of time from the second state 203-2 to the third state 203-3, the insertion section 203 does not move in the tangential direction but moves in such a manner as to extend the subject 910 in the direction normal to the tangential line. As a result, when a given point of the insertion section 203 moves, the ratio of the displacement in the tangential direction to the displacement in the moving direction is approximately equal to 0.

Figure 34:
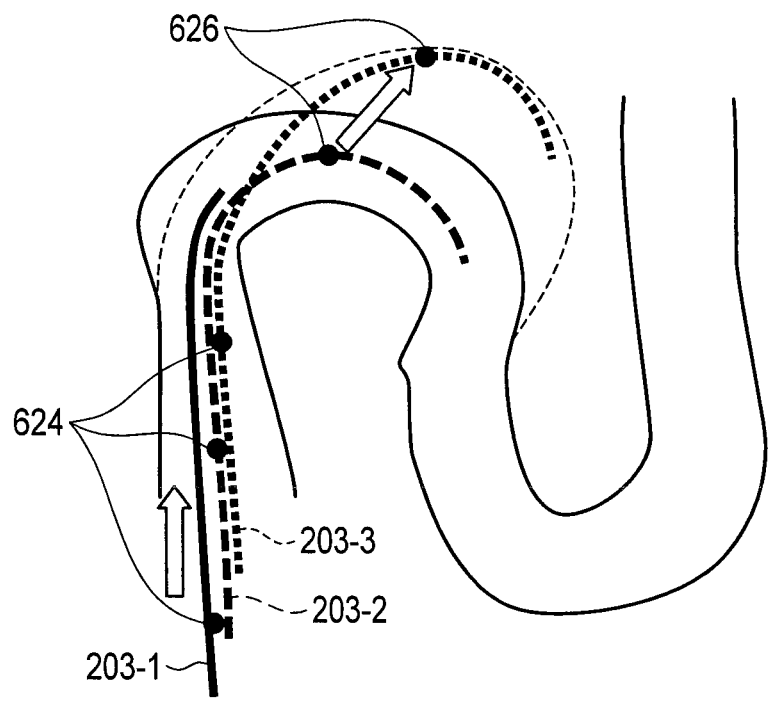
FIG. 34 schematically illustrates another example of how the insertion section is moved.

Let us assume that the insertion section 203 changes its state with time in the order of the first state 203-1, the second state 203-2 and the third state 203-3, as shown in FIG. 34. FIG. 42 shows $|\Delta Sr|/|\Delta X|$ in this case, which represents how the displacement of the insertion section 203 changes in position with time. In the period of time from the first state 203-1 to the second state 203-2, the self-following property is high, so that the ratio of the displacement of a given point in the tangential direction to the displacement of the given point in the moving direction is approximately equal to 1 when the insertion section 203 changes its position. On the other hands, in the period of time from the second state 203-2 to the third state 203-3, the insertion section 203 moves in a direction slanted with respect to the tangential direction. As a result, the ratio of the displacement of a given point in the tangential direction to the displacement of the given point in the moving direction is approximately equal to 0.5.

Where $\Delta Sr$ and $\Delta X$ are vectors, either $(\Delta Sr \cdot \Delta X)/(|\Delta Sr| \times |\Delta X|)$ or $\cos \theta$ may be used as an index ("·" is an inner product). Unlike the case where the self-following property is confirmed simply using $|\Delta Sr|/|\Delta X|$, the use of the index makes it clear that the self-following property is very low when $\Delta X$ and $\Delta Sr$ are those obtained in the movement in the opposite direction.

[Fourth State Determination Method]

In connection with the variant of the third state determination method, values used for evaluation represent how a point corresponding to an attention point in the insertion member moves in a tangential direction. The values used for evaluation may be those representing how the point moves in a direction normal to the tangential line, i.e., in a lateral direction of the insertion section 203. For example, let us assume that $\Delta Xc$ is a moving amount for which the insertion section 203 moves in a direction normal to the tangential line at an attention point as shown in FIG. 40, and that $\Delta X1$ is an amount of movement for which any point on the rear end side of the insertion section 203 moves, namely, an amount of movement for which a detection point on the rear side moves. In this case, the criterion formula representing lateral movement B is defined as follows:

$$B=|\Delta Xc|/|\Delta X1|$$

This case is expressed in FIG. 43, in which the abscissa axis represents the passage of time or the amount of movement $\Delta X1$ by which any point moves (namely the insertion amount), and the ordinate axis represents lateral movement B. That is, when the insertion section 203 is inserted normally along the subject, lateral movement B takes values which are close to 0, as indicated by the solid line. On the other hand, when the insertion section 203 is in the stick state, lateral movement B takes values close to 1.

As shown in FIG. 43, with respect to the lateral movement B, thresholds a4 and b4 can be properly determined. For example, threshold a4 may be a value in response to which a warning indicating that the subject 910 begins to extend is issued, and threshold b4 may be a value in response to which a warning indicating that further extension of the subject 910 is dangerous is issued. With the thresholds being determined properly, the value of the lateral movement B can be used as information for supporting the operation of the endoscope 200, including a warning to the user and a warning signal output to the controller 310.

The movement of an attention point of the insertion section 203 may be expressed either as a movement in the lateral direction or as a movement in the tangential direction. In either case, what is detected is the same. In either case, the amount of movement of an attention point may be compared with the amount of movement of an attention point or a detection point of the rear end portion of the insertion section 203. In addition, analysis may be made based only on the ratio of the amount of movement of a given point to its component in the tangential direction, i.e., without using the amount of movement of an attention point or a detection point on the rear end portion of the insertion section. In either case, the higher the degree of coincidence between the tangential direction of the insertion section 203 and the moving direction of the insertion section 203 is, the higher will be the self-following property of the insertion section 203. That is, the insertion section 203 can be regarded as being inserted along the subject 910. This holds true of the examples explained below.

Figure 44:
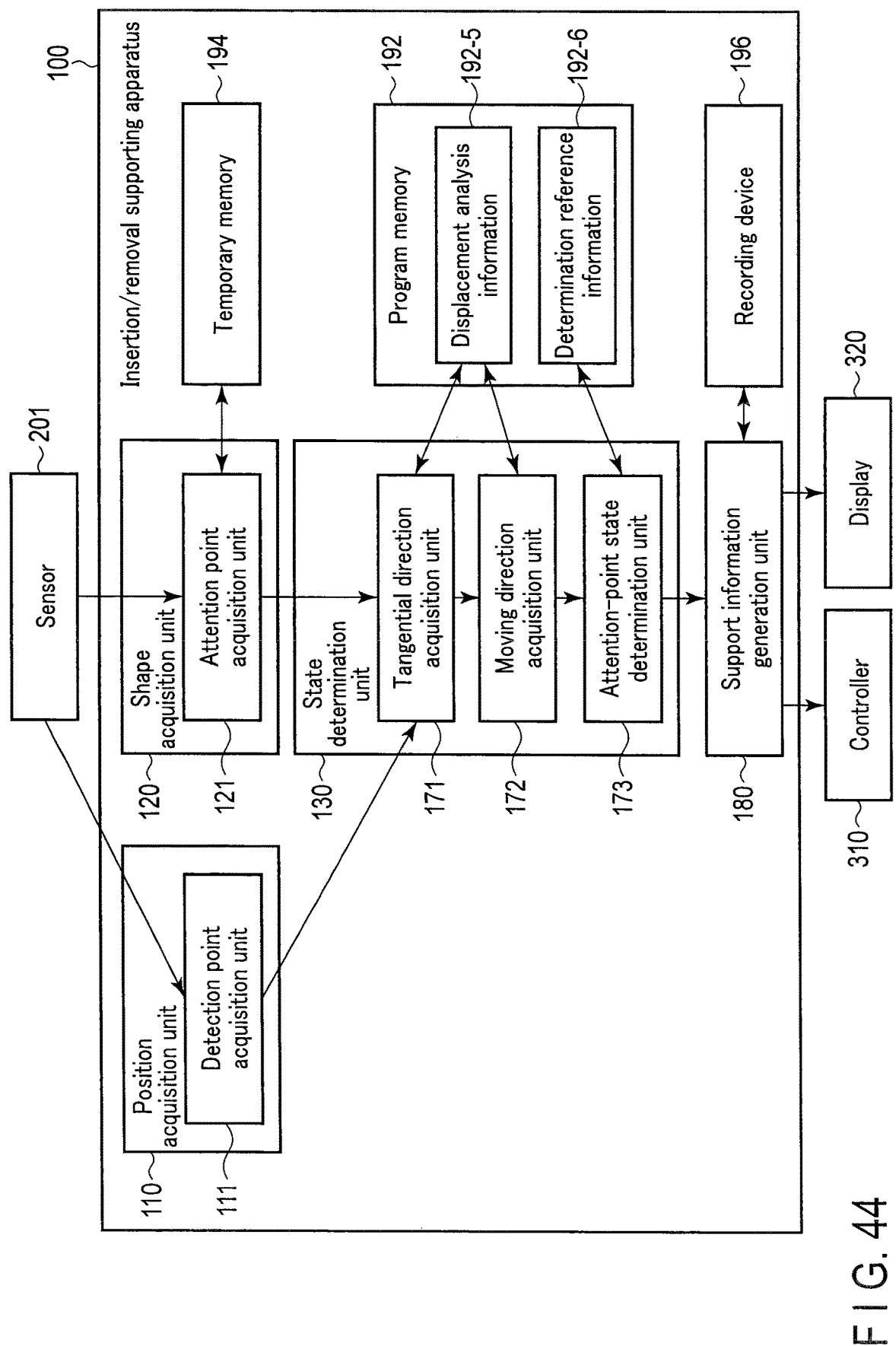
FIG. 44 is a block diagram schematically illustrating an exemplary configuration of an insertion/removal supporting apparatus employed in the fourth state determination method.

FIG. 44 schematically illustrates a configuration example of the operation supporting apparatus which can be employed for implementing the fourth state determination method. The configuration example of the operation supporting apparatus is designed to use a detection point on the rear end side.

The insertion/removal supporting apparatus 100 comprises a position acquisition unit 110, a shape acquisition unit 120, a state determination unit 130 and a support information generation unit 180. The detection point acquisition unit 111 of the position acquisition unit 110 acquires the position of a detection point where position detection on the rear end side of the insertion section 203 is performed, based on information output from the sensor 201.

The shape acquisition unit 120 acquires the shape of the insertion section 203, based on information output from the sensor 201. The attention point acquisition unit 121 of the shape acquisition unit 120 acquires the position of an attention point.

The state determination unit 130 includes a tangential direction acquisition unit 171, a moving direction acquisition unit 172 and an attention-point state determination unit 173. The tangential direction acquisition unit 171 calculates a tangential direction at an attention point of the insertion section 203, based on the shape of the insertion section 203, the position of the attention point and displacement analysis information 192-5 stored in the program memory 192. The moving direction acquisition unit 172 calculates a moving direction of an attention point, based on the position of the attention point and displacement analysis information 192-5 stored in the program memory 192. The attention point state determination unit 173 calculates a state of the attention point, based on the tangential direction at the attention point of the insertion section 203, the moving direction of the attention point and determination reference information 192-6 stored in the program memory 192.

The support information generation unit 180 generates operation support information, based on the determined state of the attention point. The operation support information is fed back to the control of the controller 310, is displayed on the display 320, or is stored in the recording device 196.

Figure 45:
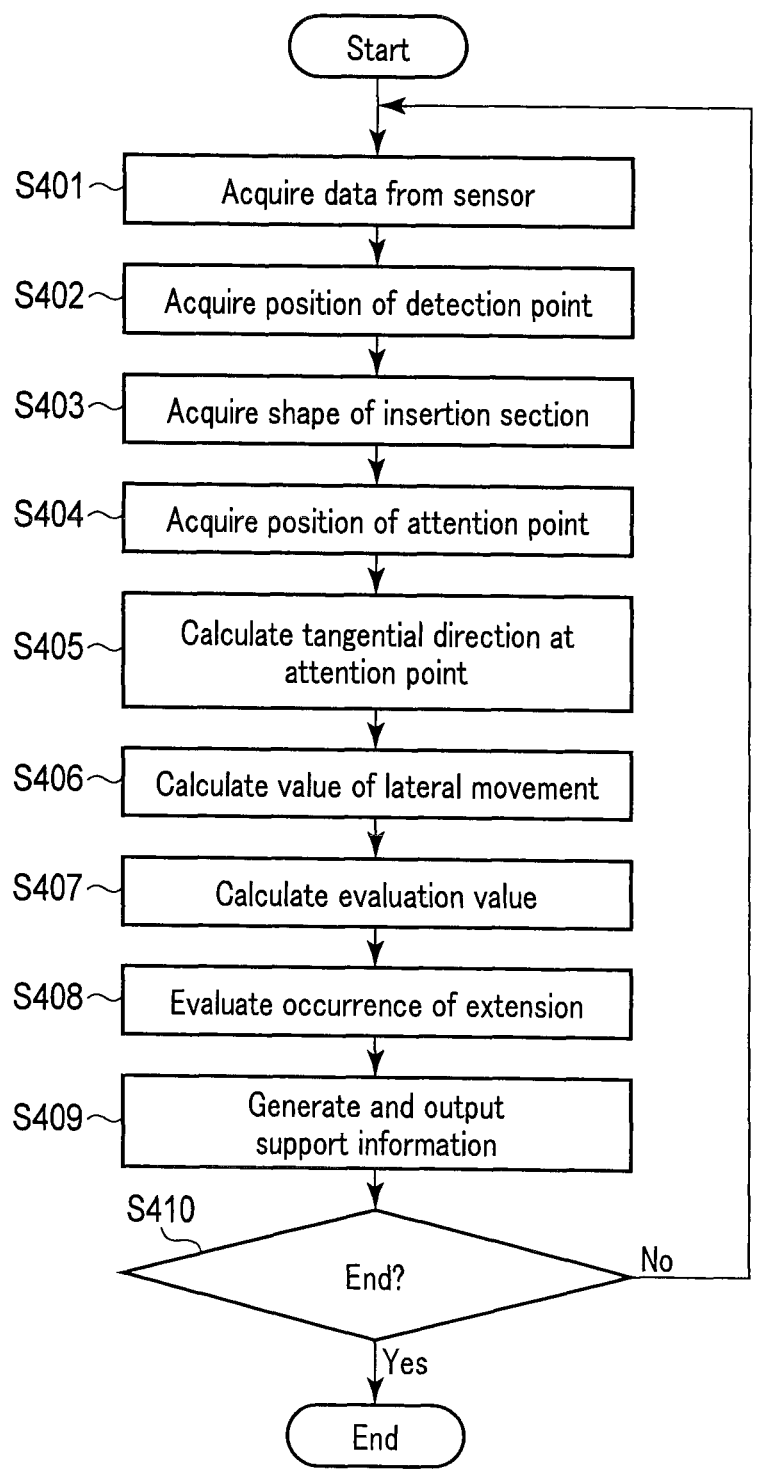
FIG. 45 is a flowchart illustrating an example of processing performed in the fourth state determination method.

How the insertion/removal supporting apparatus 100 operates in the fourth state determination method will be described with reference to the flowchart shown in FIG. 45.

In step S401, the insertion/removal supporting apparatus 100 acquires output data from the sensor 201. In step S402, the insertion/removal supporting apparatus 100 acquires the position of a rear-side detection point, based on the data acquired in step S401.

In step S403, the insertion/removal supporting apparatus 100 acquires the shape of the insertion section 203, based on the data acquired in step S401. In step S404, the insertion/removal supporting apparatus 100 acquires the position of an attention point, based on the shape of the insertion section 203 acquired in step S403.

In step S405, the insertion/removal supporting apparatus 100 calculates a tangential direction at the attention point of the insertion section 203. In step S406, the insertion/removal supporting apparatus 100 acquires a moving direction of the position of the insertion section 203 corresponding to the attention point and calculates a value representing lateral movement.

In step S407, the insertion/removal supporting apparatus 100 calculates an evaluation value representing the self-following property at the attention point of the insertion section 203, based on the positional change of the detection point and the value representing the lateral movement. Where the detection point changes in position, the smaller the value of the lateral movement is, the higher will be the self-following property.

In step S408, the insertion/removal supporting apparatus 100 perform evaluation of extension such as whether an extension occurs in the vicinity of the attention point and if the extension occurs, evaluates the degree of extension, based on the evaluation value calculated in step S407.

In step S409, the insertion/removal supporting apparatus 100 generates proper support information to be used in later processing, based on the determination result representing whether the extension of the subject occurs and on the degree of extension etc., and outputs the support information, for example, to the controller 310 and the display 320.

In step S410, the insertion/removal supporting apparatus 100 determines whether a termination signal for terminating the processing is entered. Unless the termination signal is entered, the processing returns to step S401. That is, the processing mentioned above is repeated until the termination signal is entered, and operation support information is output. If the termination signal is entered, the processing is brought to an end.

The use of the fourth state determination method enables operation support information representing whether the extension of the subject is occurred or not is generated based on the relations between the moving direction and the tangential direction at an attention point of the insertion section 203. The operation support information includes, for example, information representing the states of the insertion section 203 and subject 910, information representing whether the insertion section 203 pushes or presses the subject 910, information representing a level of pushing or pressing applied to the subject 910, and information representing whether the insertion section 203 is in an abnormal state.

In the example mentioned above, an attention point is analyzed, but this is not restrictive. Any point may be analyzed instead of the attention point. In this case, the self-following property can be evaluated based on the tangential direction at a selected point and the moving direction of the selected point.

In the above description, reference was made to the case where the self-following property is evaluated based on the relations between the amount of movement of a detection point on the rear end side of the insertion section 203 and the amount of movement of an attention point. Instead of the detection point, any attention point may be used. It should be noted that the amount of movement of the detection point does not have to be taken into account. That is, the self-following property can be evaluated based only on the ratio of the tangential-direction component of the amount of movement of an attention point to the normal-direction component of the amount of movement.

The third state determination method and the fourth state determination method are similar in that both methods evaluate the self-following property of the insertion section 203.

[Variant]

In the above example, an attention point is selected based on the shape of the insertion section 203 and how the attention point moves in a tangential direction is analyzed. The distal end of the insertion section 203 may be selected in place of the attention point, and how the distal end moves in the tangential direction may be analyzed. The tangential direction of the distal end is the direction in which the distal end of the insertion section 203 is directed.

Figure 46:
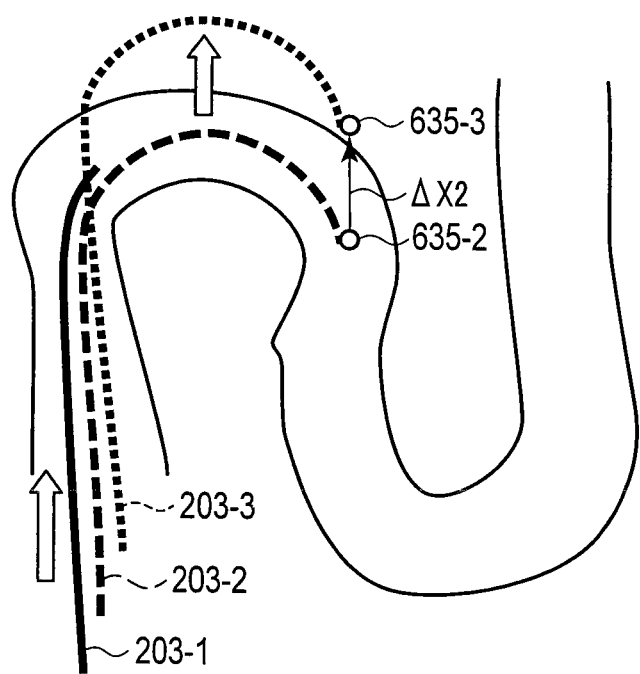
FIG. 46 illustrates a variant of the fourth state determination method and schematically illustrates an example of how an insertion section is moved.

With a state similar to that shown in FIG. 32, as shown in FIG. 46, the distal end of the insertion section 203 moves rearward from the second position 635-2 to the third position 635-3. That is, distal end retreat occurs. If the endoscope 200 is designed to acquire images in the distal end direction, whether or not the distal end of the insertion section 203 moves rearward can be detected based on the acquired images.

Distal end advance P, representing how the distal end of the insertion section 203 advances in the distal end direction, is defined by the following formula:

$$P=(\Delta X2 \cdot D)/|\Delta X1|$$

where $\Delta X2$ is a displacement vector of the distal end, D is a distal-end-direction vector, and "·" is an inner product.

Figure 47:
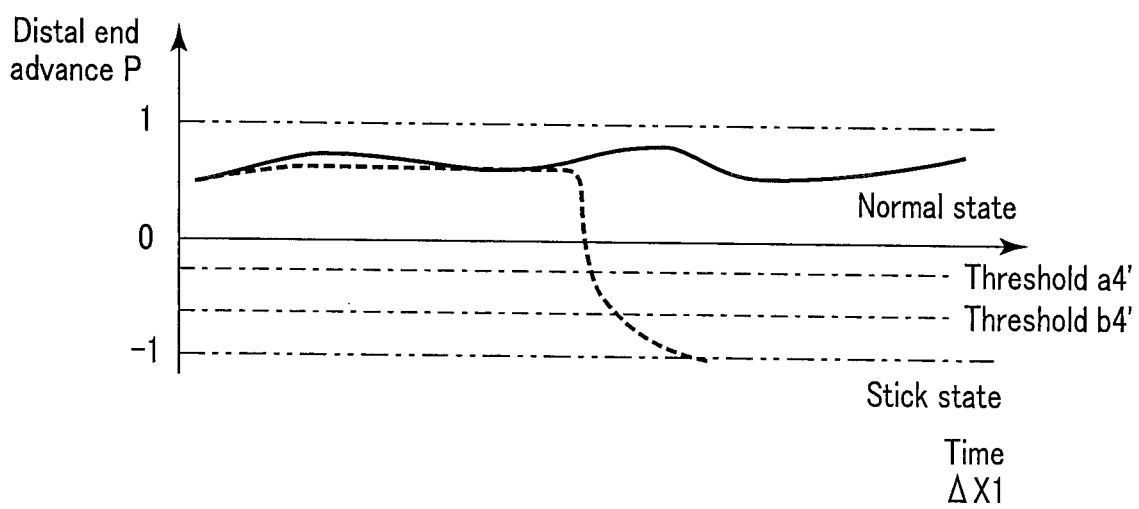
FIG. 47 illustrates an example of how the distal end advance of an insertion section changes with time.

FIG. 47 shows an example of how the distal end advance P changes in relation to the passage of time, i.e., the insertion amount $\Delta X1$ of a discretionary point on the rear end side. In FIG. 47, the solid line indicates the case where the insertion section 203 is inserted along the subject 910. In this case, the distal end of the insertion section 203 moves in the distal end direction, and the value of the distal end advance P is close to 1. In FIG. 47, the broken line indicates the case where the insertion section 203 is in the stick state. In this case, the distal end of the insertion section 203 moves rearward, and the value of the distal end advance P is close to −1.

With respect to the distal end advance P, thresholds a4' and b4' can be properly determined. For example, threshold a4' may be a value in response to which a warning indicating that the subject 910 begins to extend is issued, and threshold b4' may be a value in response to which a warning indicating that further extension of the subject 910 is dangerous is issued. With the thresholds being determined properly, the value of the distal end advance P can be used as information for supporting the operation of the endoscope 200, including a warning to the user and a warning signal supplied to the controller 310.

As described above, the state of the insertion section 203 or the state of the subject 910 can be determined based on the distal end advance P, which can be characteristically detected as indicating distal end retreat.

[First to Fourth State Determination Methods]

In each of the state determination methods described above, the degree of self-following property is evaluated. Where the amounts of movements of two or more attention points are different, a portion in which the self-following property is low exists between the attention points. When the insertion section is in the stick state, the insertion section is moving in a lateral direction, and the lateral movement indicates that the insertion section includes a portion having low self-following property.

In the first state determination method, the amount of movements of two or more attention points is detected, and if they are different, the occurrence of a buckle is determined, for example. Where the buckle occurs, a portion including the buckle has low self-following property.

In the second state determination method, an attention point is selected, and whether or not a bend of the insertion section has no self-following property is detected, namely, whether or not the bend moves laterally, pushing up the subject 910.

In the third state determination method, an attention point is selected, and the self-following property is evaluated based on how the position of the attention point changes in the insertion section 203. In the evaluation of the self-following property, use is made of the phenomenon that when the self-following property is high, the position of an attention point of the insertion section 203 is determined by the insertion amount.

In the fourth state determination method, the self-following property is evaluated based on the tangential line of a given point and the moving direction of the given point. In the evaluation of the self-following property, use is made of the phenomenon that when the self-following property is high, a given point moves in the tangential direction of the shape of the insertion section 203. When the self-following property is low, lateral movement takes place.

The state where the self-following property is low can be regarded as a state where lateral movement is occurring. Therefore, it can be said that each of the above state determination methods evaluates the degree of lateral movement.

Portions which attention should be paid to within the insertion section 203 or the subject 910 are those which are located in a flexure of the subject 910. In the flexure of the subject 910, the insertion section 203 is likely to have low self-following property and move laterally in the flexure, pushing the wall of the subject. It is therefore significant to evaluate the state of the insertion section 203 in the flexure of the subject or the state of the flexure of the subject. In the second, third and fourth state determination methods, therefore, a flexure is regarded as an attention point and is analyzed.

However, this is not restrictive. Various portions can be regarded as attention points, and the state of the insertion section 203 or the state of the subject 910 can be analyzed at such attention points in a method similar to that described above.

As can be seen from the above, the displacement information acquisition method 141 and the interrelation calculation unit 142; the displacement acquisition unit 151, 161 and the displacement information calculation unit 152, 162; or the tangential direction acquisition unit 171 and the moving direction acquisition unit 172 function as a self-following property evaluation unit for evaluating the self-following property in an inserted condition of the insertion section 203. The buckle determination unit 143 or the attention-point state determination unit 153, 163, 173 functions as a determination unit for determining the state of the insertion section 203 or subject 910 based on the self-following property.

The state of the insertion section 203 or subject 910 is not used solely for determining whether the insertion section 203 is inserted along the subject 910. When inserting the insertion section 203 into the subject 910, the user may intentionally change the shape of the subject. For example, the user may operate the insertion section 203 in such a manner that a flexure of the subject 910 is made substantially straight and the insertion section 203 can easily move through the flexure. In such an operation as well, information representing the shape of the insertion section 203, the shape of the subject 910, the force with which the insertion section 203 presses the subject 910, etc. is useful to the user.

[Combination of First to Fourth State Determination Methods]

The first to fourth state determination methods can be used in combination. For example, where the first state determination method is combined with another state determination method, the following advantages are obtained. The use of the first state determination method enables acquisition of information regarding a buckle occurring in the insertion section 203. By subtracting the displacement components resulting from the buckle, the accuracy of the operation results obtained in the second to fourth state determination methods can be improved, and the user can accurately understand what is happening to the insertion section 203. Where the first to fourth state determination methods are used in combination, the amount of information obtained thereby is larger than the amount of information obtained in each method. This is effective in enhancing the accuracy of support information to be generated.

[Operation Supporting Information]

The support information generation unit 180 generates operation support information, using information obtained in the first to fourth state determination methods and representing the state of the insertion section 203 or the state of the subject 910. The operation support information is information for supporting the user when the user inserts the insertion section 203 into the subject 910.

The operation support information is generated by not only the information obtained in the first to fourth state determination methods and representing the state of the insertion section 203 or the state of the subject 910, but also information on combination of various kinds of information, including information entered from the input device 330 and information supplied from the controller 310. Necessary information can be acquired by properly using the first to fourth state determination methods in combination.

The operation support information is displayed, for example, on the display 320, and the user operates the endoscope 200 while taking indication of the display into consideration. The operation support information is fed back to the control of the controller 310. Since this enables the controller 310 to adequately control the endoscope 200, the user's operation of the endoscope 200 can be supported. The use of the operation support information enables smooth operation of the endoscope 200.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A supporting apparatus for supporting insertion of a flexible insertion member into a subject and removal thereof, the supporting apparatus comprising:
    a controller comprising hardware, the controller being configured to:
        determine a first attention point on the insertion member while within the subject at a first time based on a first calculated shape of the insertion member at the first time, the first attention point being a characteristic point determined based on the shape of the insertion member at the first time,
        after a displacement of the insertion member within the subject, at a second time after the first time, determine a new first attention point based on a second calculated shape of the insertion member at the second time, the new first attention point being the characteristic point determined based on shape of the insertion member at the second time;
        determine a first displacement between the first attention point and the new first attention point;
        determine a second displacement of at least one rear-side attention point fixed to the insertion member, the second displacement being from the first time to the second time, the second displacement being along a predetermined portion in a longitudinal direction of the insertion member;
        calculate a relationship between the first displacement and the second displacement;
        determine a state of the insertion member or the subject based on the calculated relationship; and
        determines that a level of abnormality of the state of the insertion member or the subject increases as a ratio of the first displacement to the second displacement increases.

2. The supporting apparatus according to claim 1, wherein the controller determines that the smaller the first displacement is, the more proper the insertion member is inserted along the subject.

3. The supporting apparatus according to claim 1, wherein the first attention point and new first displacement are determined based on a bending portion of the insertion member.

4. The supporting apparatus according to claim 3, wherein the first attention point and new first displacement are each turn-around points of the bending portion of the insertion member.

5. The supporting apparatus according to claim 1, wherein the state to be determined includes a state representing whether or not the insertion member extends the subject at a position corresponding to the new first attention point.

6. The supporting apparatus according to claim 1, wherein the state to be determined includes a state where the insertion member pushes or presses the subject.

7. The supporting apparatus according to claim 1, further comprising:
    a plurality of position sensors arranged in the insertion member,
    wherein the controller calculates the shape of the insertion member at the first time and at the second time, based on detection results of the position sensors, and calculates the positions of the first attention point and the new first attention point, based on the calculated shape of the insertion member at the first time and at the second time and the detection results of the position sensors, and
    determines the first displacement, based on the position corresponding to the new first attention point.

8. The supporting apparatus according to claim 1, further comprising:
    an insertion amount sensor configured to be arranged at an insertion port of the subject and to detect an insertion amount of the insertion member; and
    a shape sensor which acquires information on the shape of the insertion member at the first time and at the second time,
    wherein the controller calculates the shape of the insertion member at the first time and at the second time, based on a detection result of the shape sensor, and calculates positions of the first attention point and the new first attention point, based on the calculated shape of the insertion member at the first time and at the second time and the detection result of the insertion amount sensor, and
    determines the first displacement, based on the position of the new first attention point.

9. The supporting apparatus according to claim 1, further comprising:
  a position sensor arranged at the insertion member; and
  a shape sensor which acquires information on the shape of the insertion member at the first time and at the second time,
  wherein the controller calculates the shape of the insertion member at the first time and at the second time, based on a detection result of the shape sensor, and calculates positions of the first attention point and the new first attention point, based on the calculated shape of the insertion member at the first time and at the second time and the detection result of the position sensor, and determines the first displacement, based on the position of the new first attention point.

10. The supporting apparatus according to claim 1, further comprising:
  a position sensor arranged at the insertion member,
  wherein the controller determines the second displacement, based on detection results of the position sensor.

11. The supporting apparatus according to claim 1, further comprising:
  an insertion amount sensor configured to be arranged at an insertion port of the subject and to detect an insertion amount of the insertion member; and
  a shape sensor which acquires information on the shape of the insertion member at the first time and at the second time,
  wherein the controller determines the second displacement, based on detection results of the insertion amount sensor and detection results of the shape sensor.

12. The supporting apparatus according to claim 1, further comprising:
  a position sensor arranged at the insertion member; and
  a shape sensor which acquires information on the shape of the insertion member at the first time and at the second time,
  wherein the controller determines the second displacement, based on detection results of the position sensor and detection results of the shape sensor.

* * * * *